(12) United States Patent  
Barreca et al.

(10) Patent No.: US 10,738,013 B2
(45) Date of Patent: Aug. 11, 2020

(54) ELUXADOLINE CRYSTALLINE FORMS AND PROCESSES FOR THEIR PREPARATION

(71) Applicant: Quimica Sintetica, S.A., Barcelona (ES)

(72) Inventors: Giuseppe Barreca, Montevecchia (IT); Giampiero Ventimiglia, Francavilla Fontana (IT); Norberto Masciocchi, Como (IT)

(73) Assignee: Quimica Sintetica, S.A., Barcelona (ES)

( * ) Notice: Subject to any disclaimer, the term of this patent is extended or adjusted under 35 U.S.C. 154(b) by 0 days.

(21) Appl. No.: 16/481,297

(22) PCT Filed: Jan. 26, 2018

(86) PCT No.: PCT/EP2018/051975
§ 371 (c)(1),
(2) Date: Jul. 26, 2019

(87) PCT Pub. No.: WO2018/138274
PCT Pub. Date: Aug. 2, 2018

(65) Prior Publication Data
US 2019/0345114 A1    Nov. 14, 2019

(30) Foreign Application Priority Data

Jan. 27, 2017  (EP) ..................... 17382038
Dec. 4, 2017   (EP) ..................... 17382833

(51) Int. Cl.
*C07D 233/56*     (2006.01)
(52) U.S. Cl.
CPC ........ *C07D 233/56* (2013.01); *C07B 2200/13* (2013.01)
(58) Field of Classification Search
None
See application file for complete search history.

(56) References Cited

FOREIGN PATENT DOCUMENTS

WO    WO 2017/015606    1/2017

OTHER PUBLICATIONS

International Search Report corresponding to International application No. PCT/EP2018/051975 dated Jun. 20, 2018.
International Preliminary Report on Patentability corresponding to International application No. PCT/EP2018/051975 dated Jul. 30, 2019.
Written Opinion of the International Searching Authority corresponding to International Application No. PCT/EP2018/051975 dated Jun. 20, 2018.

*Primary Examiner* — Samantha L Shterengarts
(74) *Attorney, Agent, or Firm* — Jenkins, Wilson, Taylor & Hunt, P.A.

(57) ABSTRACT

Novel crystalline forms of Eluxadoline, having the formula (I), are described. Also described are the processes for the preparation of said crystalline forms.

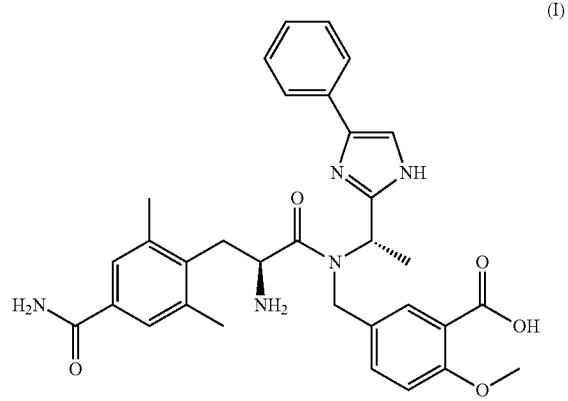

16 Claims, 20 Drawing Sheets

FIG 15
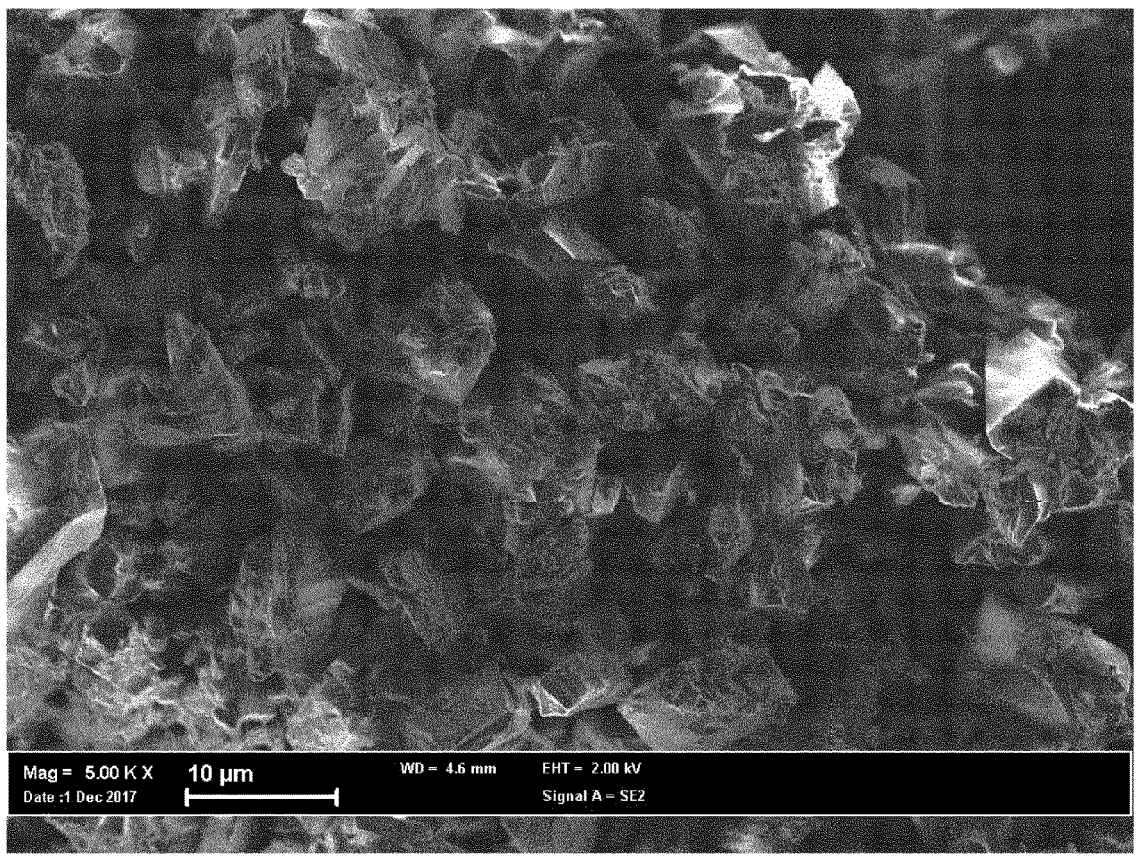
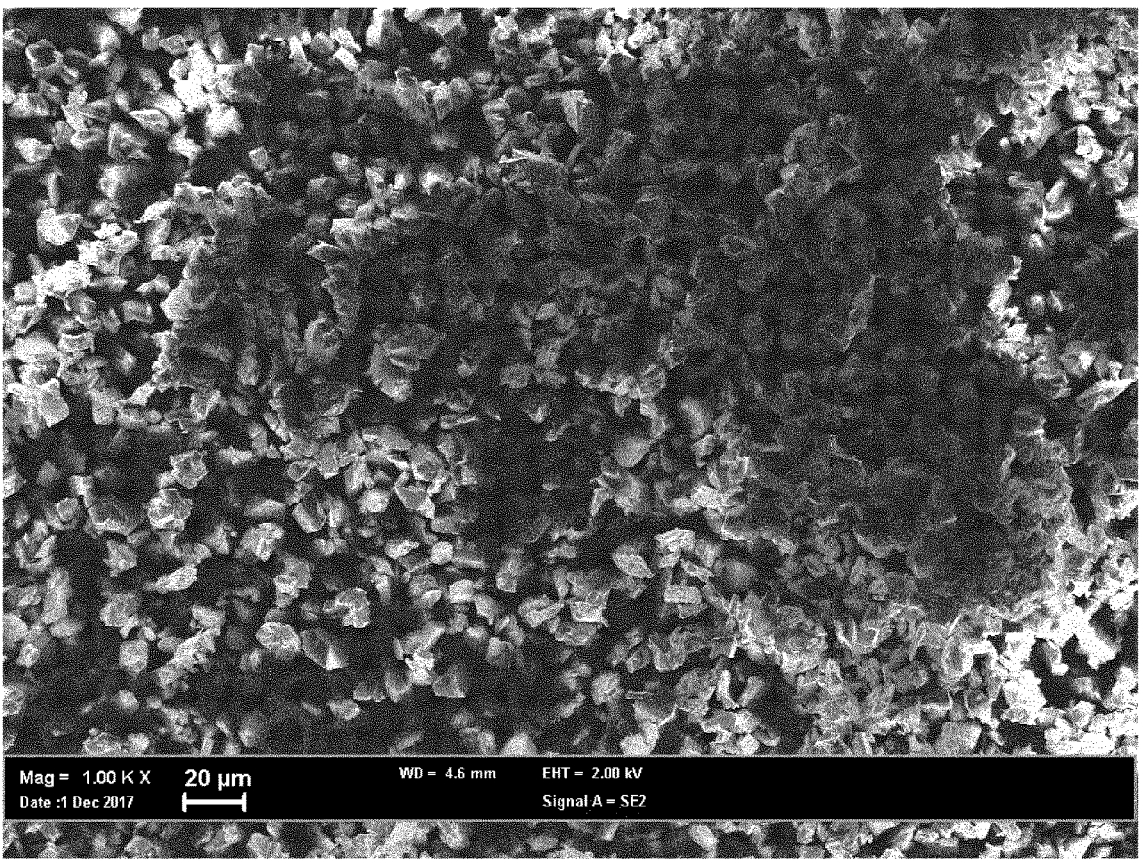

ELUXADOLINE CRYSTALLINE FORMS AND PROCESSES FOR THEIR PREPARATION

FIELD OF THE INVENTION

The present invention relates to new crystalline forms of eluxadoline, to the processes for their preparation and to their use in the preparation of other solid forms of eluxadoline.

STATE OF THE ART

Eluxadoline is the INN denomination assigned to the compound having IUPAC name 5-({[(2S)-2-amino-3-(4-carbamoyl-2,6-dimethylphenyl)propanoyl][(1S)-1-(4-phenyl-1H-imidazol-2-yl)ethyl]amino}methyl)-2-methoxybenzoic acid and the formula reported below:

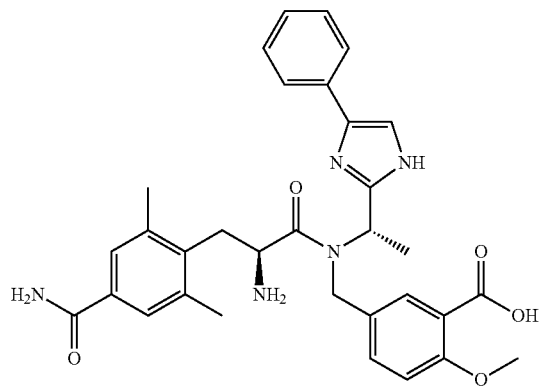 [SMILES: COc1ccc(CN(C(=O)[C@@H](N)Cc2c(C)cc(C(N)=O)cc2C)[C@@H](C)c2nc(-c3ccccc3)c[nH]2)cc1C(=O)O]

Eluxadoline is a μ- and κ-opioid receptor agonist and δ-opioid receptor antagonist that acts locally in the enteric nervous system. The drug, administered orally, is active locally in the intestine and is able to control gastrointestinal function (GI) and at the same time to reduce the pain and mitigate the effect of constipation. Its use has been approved for the treatment of diarrhea and abdominal pain in individuals with diarrhea-predominant irritable bowel syndrome (IBS-D).

The family of compounds to which eluxadoline belongs is disclosed in patent application WO 2005/090315 A1, while patent application WO 2006/099060 A2 is directed to processes for the preparation of these compounds.

As generally known, any active principle may exist under amorphous or different crystalline forms (polymorphs), either as pure compound or in forms in which, in the structure of the crystal, are present molecules of water (hydrates) or of another solvent (solvates); besides, in case of hydrates and solvates, the ratio between the number of molecules of active principle and molecules of water or solvent may vary, giving rise to different solid forms of the compound.

Different salts and solid-state forms of an active pharmaceutical ingredient may possess different properties. Such variations in the properties of different salts and solid-state forms may provide a basis for improving formulation, for example, by facilitating better processing or handling characteristics, changing the dissolution profile in a favourable direction, or improving stability (polymorphic and/or chemical) and shelf-life. These variations in the properties of different salts and solid-state forms may also offer improvements to the final dosage form, for instance, if they serve to improve bioavailability. Different salts, solid-state forms and solvates of an active pharmaceutical ingredient may also give rise to a variety of polymorphs or crystalline forms, which, in turn, may provide additional opportunities to assess variations in the properties and characteristics of a solid active pharmaceutical ingredient.

While not intending to be bound by any theory, certain solid forms are characterized by physical properties, e.g., stability, solubility and dissolution rate, appropriate for pharmaceutical and therapeutic dosage forms. Moreover, while not wishing to be bound by any theory, certain solid forms are characterized by physical properties (e.g., density, compressibility, hardness, morphology, cleavage, stickiness, solubility, water uptake, electrical properties, thermal behaviour, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using analytical chemical techniques, including solid-state analytical techniques (e.g., X-ray diffraction, microscopy, spectroscopy and thermal analysis), as described herein and known in the art.

For these reasons, chemical compounds useful in the pharmaceutical field are systematically screened looking for the physical form(s) that present an improved set of production, storage and handling properties, and which result in an improved administration to the patients.

Patent application WO 2009/009480 A2 discloses two crystalline forms of eluxadoline, referred to in the document respectively as Form α and Form β. Form α is characterized by an X-ray powder diffraction pattern having the main peaks at about 10.2°, 11.3°, 11.8°, 14.0°, 14.3°, 14.7°, 16.1 and 18.3° 2θ, while Form 1 is characterized by an X-ray powder diffraction pattern having the main peaks at about 11.0°, 12.4°, 14.9°, 15.2°, 22.1°, 25.6°, 27.4°, and 30.4° 2θ.

Patent application WO 2017/015606 A1 discloses several crystalline forms of eluxadoline, referred to therein as Form I, Form II, Form III, and Form IV. Form I is characterized by an X-ray powder diffraction pattern having peaks at about 6.4°, 7.5°, 9.1°, 10.0°, and 13.0° 2θ. Form II is characterized by an X-ray powder diffraction profile having peaks at about 7.2°, 11.6°, 12.1°, 12.7° and 16.9° 2θ. Form III is characterized by an X-ray powder diffraction pattern having peaks at about 9.3°, 10.2°, 11.5°, 13.3° and 21.8° 2θ. Form IV is characterized by an X-ray powder diffraction profile having peaks at about 9.3°, 10.2°, 11.5°, 13.3° and 21.8° 2θ.

However, no information is provided in any of these documents about any useful properties from the standpoint of the pharmaceutical industry, neither regarding ease of handling of the forms in the production of formulations nor regarding the storage stability (polymorphic and/or chemical) of eluxadoline when prepared in one of these crystalline forms.

An object of the present invention is the provision of a novel process for the preparation of a polymorphic form α' of eluxadoline (as defined hereinbelow) which, surprisingly, is polymorphically and chemically stable. Since this polymorphic form represents a valuable product, it is an object that upscaling of this process, in order to meet the needs of industrial-scale production, should be easily accomplishable. It is a further object of the present invention that said novel process should produce high-purity products which must contain as low an amount of possibly harmful compounds as possible.

Surprisingly, it was found that new solvate forms E of eluxadoline allow for the realization of this process and, thus, of the new polymorphically and chemically stable crystalline form α'. It was found that in terms of the starting material from which the solvate forms E of eluxadoline can be produced, they are extremely flexible.

Further, it was found that the reaction conditions necessary to produce these solvate forms are highly advantageous in terms of energy consumption in combination with the chemical nature of the solvents used.

SUMMARY OF THE INVENTION

These objectives are achieved with the present invention that, in a first aspect thereof, relates to a solvate form of 5-({[(2S)-2-amino-3-(4-carbamoyl-2,6-dimethylphenyl) propanoyl][(1S)-1-(4-phenyl-1H-imidazol-2-yl)ethyl] amino}methyl)-2-methoxybenzoic acid (eluxadoline) with a ketone selected from the group consisting of acetone, 2-butanone, 3-pentanone and mixtures thereof.

In a second aspect thereof, the invention relates to a process for producing said solvate form of eluxadoline.

In a third aspect thereof, the invention relates to the use of said solvate form for producing other solid forms of eluxadoline. In an embodiment, the invention relates to the use of said solvate form for producing the crystalline Form α (as defined in WO 2009/009480 A2).

According to a further aspect thereof, this invention relates to a process for preparing a polymorphically and chemically stable crystalline Form α' of eluxadoline comprising heating the solvate form object of the first aspect of the invention to a temperature from 20° C. to 60° C.

The present invention also relates to a polymorphically and chemically stable crystalline Form α' of eluxadoline. Moreover, the invention relates to a pharmaceutical composition comprising, as active ingredient, an effective amount of the crystalline forms of the invention and at least one pharmaceutically acceptable excipient.

The invention further relates to said crystalline forms or to the pharmaceutical compositions comprising them for use in therapy.

BRIEF DESCRIPTION OF THE DRAWINGS

FIG. 15 shows two SEM images of the polymorphically and chemically stable form α' of eluxadoline.

DETAILED DESCRIPTION OF THE INVENTION

Figure 1:
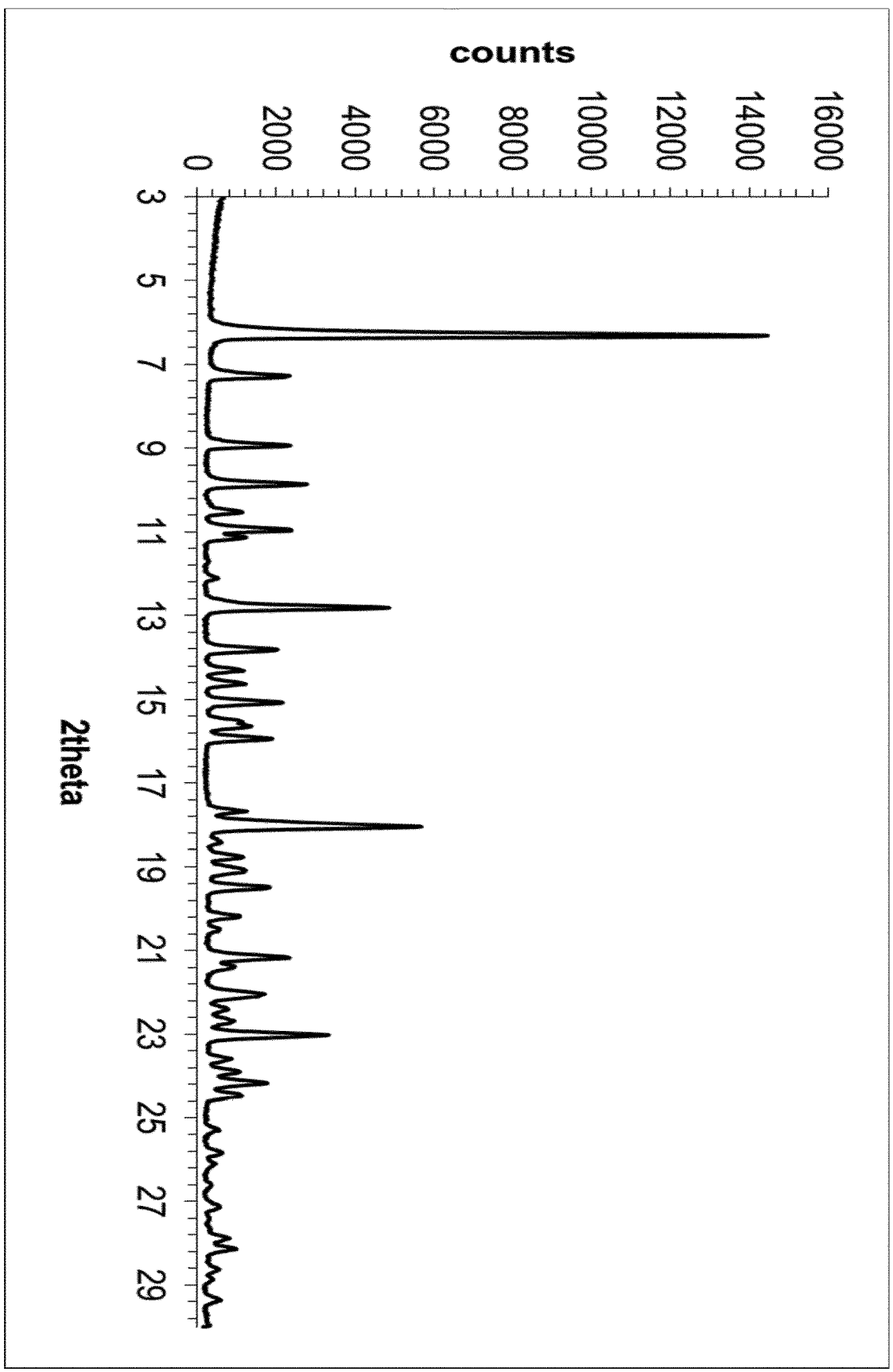
FIG. 1 depicts the X-Ray powder diffractogram of the solvate form $\varepsilon_1$ of eluxadoline.

All terms used in this application, unless otherwise specified, are to be understood in their ordinary meaning as known in the technical field. Other more specific definitions of certain terms used in this application are listed below and are intended to be applied uniformly to the entire application, unless indicated otherwise.

The term "about" includes the range of experimental errors, which can normally occur performing a measurement.

The term "excipient" means any substance contained in the final pharmaceutical form other than the active ingredient and which generally may not be therapeutically effective by itself. Excipients are essential for the administration of the active substance, as they allow to deliver the drug to the target site. Excipients are commonly referred to as raw materials entering into the composition of a pharmaceutical preparation with the aim of giving a shape, to facilitate administration and preserve the active ingredient. Furthermore, they contribute to characterize the pharmaceutical preparation from the point of view of appearance, stability, biopharmaceutical profile and acceptability by the patient.

By "polymorphically stable" it is meant that the crystalline Form α' of the present invention when stored under stressed conditions i.e., up to a temperature of 120° C. for 24 or 48 hours, show no signs of crystallinity associated to other polymorphs of eluxadoline (e.g. Form β) as judged by the absence of their relevant peaks in an X-ray powder diffractogram (XRPD).

By "chemically stable" it is meant that the crystalline Form α' of the present invention shows a reduced degradation upon storage under stressed conditions, i.e. when stored at a temperature of up to 120° C. for 24 or 48 hours. Reduced degradation means that a HPLC analysis of eluxadoline stored at 120° C. for 24 hours shows a content of the impurity at relative retention time 1.11, as detectable using the HPLC method reported below, lower than 50%, preferably lower than 40%, more preferably lower than 30%, even more preferably lower than 20%. Reduced degradation also means that a HPLC analysis of eluxadoline stored at 120° C. for 48 hours shows a content of the impurity at relative retention time 1.11, as detectable using the HPLC method reported below, lower than 60%, preferably lower than 50%, more preferably lower than 40%, even more preferably lower than 30%.

The parameters most commonly used to describe the particle size distribution of powders are the $D_{10}$, $D_{50}$ and $D_{90}$ values.

The terms $D_{10}$, $D_{50}$, and $D_{90}$ as discussed herein are known to those skilled in the art. $D_{50}$ refers to the maximum particle diameter below which 50% of the sample volume exists. $D_{90}$ refers to the maximum particle diameter below which 90% of the sample volume exists. $D_{10}$ refers to the maximum particle diameter below which 10% of the sample volume exists. The values of $D_{10}$, $D_{50}$ and $D_{90}$ are expressed as diameter; for non-spherical particles, the Malvern® Mastersizer 2000, using an internal algorithm of the instrument, relates the particle size to that of spheres. The term particle size distribution span refers to the result of the calculation $[(D_{90}-D_{10})/D_{50}]$.

It has been found that the polymorphic forms of eluxadoline prepared according to the present invention are crystalline as determined by means of XRPD, and show complex DSC profiles. Such crystalline forms undergo thermal transitions involving desolvation/dehydration processes and subsequent melting of desolvated/dehydrated forms characterized by their DSC melting peak temperatures. Further thermal transitions may follow when e.g. degradation occurs. It will be understood that the onset and/or peak temperature values of the DSC may vary slightly from one machine to another, one method to another or from one sample to another, and so the values quoted are not to be construed as absolute. In fact, the observed temperatures will depend on the rate of temperature change as well as sample preparation technique and the particular instrument employed. It will be estimated and taken into account that the temperature values obtained applying such different conditions may have a ±4° C. accuracy.

In its first aspect, the invention relates to a solvate form of eluxadoline—as determined by, e.g., $^1$H NMR analysis—wherein said solvate form is formed with a ketone selected from the group consisting of acetone, 2-butanone, 3-pentanone and mixtures thereof.

Solvates of a crystalline solid include one or more molecule of solvent in the interstices or voids of the crystal network. The filling of the voids of the crystalline structure with one or more solvent species (e.g. acetone, 2-butanone or 3-pentanone) takes place according to the molar volume of the guest molecule and the empty space of the host structure, also taking into account the possibility to form a network of hydrogen bonding. The term "solvate" refers to a molecular complex comprising eluxadoline or a derivative thereof and a stoichiometric or non-stoichiometric amount of a ketone selected from the group consisting of acetone, 2-butanone, 3-pentanone and mixtures thereof.

Preferably, the new solvate form of eluxadoline—for brevity referred to in the rest of the description and in the claims as form ε (epsilon)—is:
(i) a solvate with acetone (referred to in the following as form $ε_1$) showing unit cell parameters substantially equal to the following cell dimensions: a=24.18 Å±0.01 Å; b=17.10 Å±0.01 Å, c=9.62 Å±0.01 Å; α=90 degrees, β=90 degrees; γ=90 degrees;
(ii) a solvate with 2-butanone (referred to in the following as form $ε_2$) showing unit cell parameters substantially equal to the following cell dimensions a=24.17 Å±0.01 Å; b=17.05 Å±0.01 Å, c=9.69 Å±0.01 Å; α=90 degrees, β=90 degrees; γ=90 degrees; or
(iii) a solvate with 3-pentanone (referred to in the following as form $ε_3$) showing unit cell parameters substantially equal to the following cell dimensions a=23.88 Å±0.01 Å; b=17.13 Å±0.01 Å, c=9.76 Å±0.01 Å; α=90 degrees, β=90 degrees; γ=90 degrees;

wherein measurement of said solvate form is at a temperature of 25° C.

More preferably said solvate form $ε_1$ shows an X-ray powder diffraction pattern that, when collected with the Kα radiation of copper (λ=1.5418 Å), is characterized by main peaks at:
(iv) 6.33°, 8.92°, 9.86°, 12.80° and 18.04°±0.10° 2θ; or
(v) 6.33°, 7.28°, 8.92°, 9.86°, 12.80°, 13.82°, 15.06°, and 18.04°±0.10° 2θ.

Even more preferably said solvate form $ε_1$ shows an X-ray powder diffraction pattern that, when collected with the Kα radiation of copper (λ=1.5418 Å), is characterized by at least 5 peaks (±0.1° 2θ) selected from Table 1A or 1B:

TABLE 1A

| °2θ | d space (Å) | $I_{rel}$ (%) |
|---|---|---|
| 6.30 | 14.0181 | 100 |
| 7.28 | 12.1331 | 18 |
| 8.92 | 9.9057 | 17 |
| 9.86 | 8.9634 | 21 |
| 10.94 | 8.0808 | 18 |
| 12.80 | 6.9104 | 35 |
| 13.82 | 6.4026 | 15 |
| 15.06 | 5.8781 | 16 |
| 15.94 | 5.5555 | 14 |
| 18.04 | 4.9133 | 42 |
| 19.48 | 4.5532 | 14 |
| 21.16 | 4.1953 | 17 |
| 22.04 | 4.0298 | 13 |
| 23.02 | 3.8604 | 25 |
| 24.16 | 3.6808 | 13 |

TABLE 1B

| °2θ | d space (Å) | $I_{rel}$ (%) |
|---|---|---|
| 6.30 | 14.0181 | 100 |
| 7.28 | 12.1331 | 18 |
| 8.92 | 9.9057 | 17 |
| 9.86 | 8.9634 | 21 |
| 10.52 | 8.4025 | 8 |
| 10.94 | 8.0808 | 18 |
| 12.80 | 6.9104 | 35 |
| 13.82 | 6.4026 | 15 |
| 14.30 | 6.1888 | 8 |
| 14.62 | 6.0540 | 9 |
| 15.06 | 5.8781 | 16 |
| 15.64 | 5.6614 | 10 |
| 15.94 | 5.5555 | 14 |
| 17.66 | 5.0181 | 8 |
| 18.04 | 4.9133 | 42 |
| 18.76 | 4.7263 | 9 |
| 19.08 | 4.6477 | 9 |
| 19.48 | 4.5532 | 14 |
| 20.18 | 4.3968 | 8 |
| 21.16 | 4.1953 | 17 |
| 22.04 | 4.0298 | 13 |
| 23.02 | 3.8604 | 25 |
| 24.16 | 3.6808 | 13 |
| 24.46 | 3.6363 | 8 |

Figure 2:
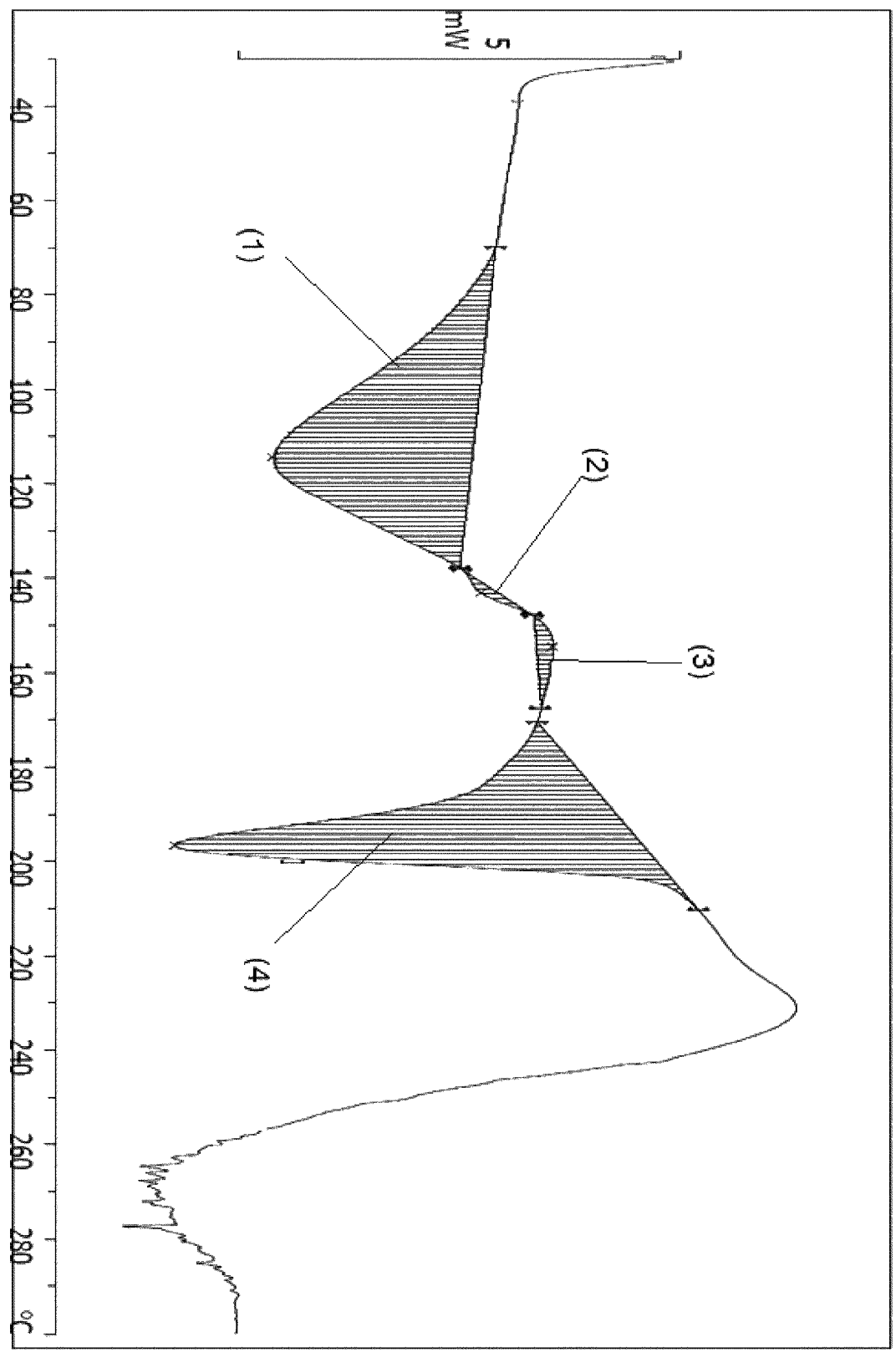
FIG. 2 provides a DSC thermogram of the solvate form $\varepsilon_1$ of eluxadoline.

The solvate form $ε_1$ is further characterized by:
1. a DSC thermogram showing a feature between 69.7° C. and 137.7° C. (with a maximum at 114.2° C.), an event between 138.1° C. and 147.8° C. (with a maximum at 143.1° C.), a feature between 147.9° C. and 167.5° C. (with a maximum at 154.4° C.) and an event between 170.3° C. and 210.5° C. (with a maximum at 196.4° C.); FIG. 2 shows these different features (1) to (4), wherein (1) has Integral −449.02 mJ, normalized −64.61 Jg$^{-1}$, Onset 84.26° C.; (2) has Integral −5.92 mJ, normalized −0.85 Jg$^{-1}$, Onset 138.15° C.; (3) has Integral 13.66 mJ, normalized 1.97 Jg$^{-1}$, Onset 147.97° C.; (4) has Integral −418.27 mJ, normalized −60.18 Jg$^{-1}$, Onset 184.04° C.; and/or 2. a TGA thermogram showing a weight loss step between 25° C. and 90° C. of up to 16.0%.

Preferably, solvate form $\varepsilon_2$ shows an X-ray powder diffraction pattern that, when collected with the Kα radiation of copper (λ=1.5418 Å), is characterized by main peaks at:
(vi) 6.32°, 8.94°, 10.98°, 12.78° and 18.02°±0.10° 2θ; or
(vii) 6.32°, 8.94°, 9.80°, 10.98°, 12.78°, 13.80°, 15.10° and 18.02°±0.10° 2θ.

Even more preferably said solvate form $\varepsilon_2$ shows an X-ray powder diffraction pattern that, when collected with the Kα radiation of copper (λ=1.5418 Å), is characterized by at least 5 peaks (±0.1° 2θ) selected from Table 2A or 2B:

TABLE 2A

| °2θ | d space (Å) | I$_{rel}$ (%) |
| --- | --- | --- |
| 6.32 | 13.9738 | 100 |
| 8.94 | 9.8836 | 17 |
| 9.80 | 9.0181 | 14 |
| 10.98 | 8.0514 | 18 |
| 12.78 | 6.9212 | 34 |
| 13.80 | 6.4118 | 15 |
| 15.10 | 5.8626 | 16 |
| 15.98 | 5.5417 | 15 |
| 18.02 | 4.9187 | 43 |
| 23.02 | 3.8604 | 22 |

TABLE 2B

| °2θ | d space (Å) | I$_{rel}$ (%) |
| --- | --- | --- |
| 6.32 | 13.9738 | 100 |
| 7.28 | 12.1331 | 12 |
| 8.94 | 9.8836 | 17 |
| 9.80 | 9.0181 | 14 |
| 10.98 | 8.0514 | 18 |
| 12.78 | 6.9212 | 34 |
| 13.80 | 6.4118 | 15 |
| 15.10 | 5.8626 | 16 |
| 15.56 | 5.6903 | 10 |
| 15.98 | 5.5417 | 15 |
| 18.02 | 4.9187 | 43 |
| 19.02 | 4.6623 | 9 |
| 19.48 | 4.5532 | 10 |
| 21.16 | 4.1953 | 14 |
| 22.02 | 4.0334 | 13 |
| 23.02 | 3.8604 | 22 |
| 24.10 | 3.6898 | 12 |

Figure 5:
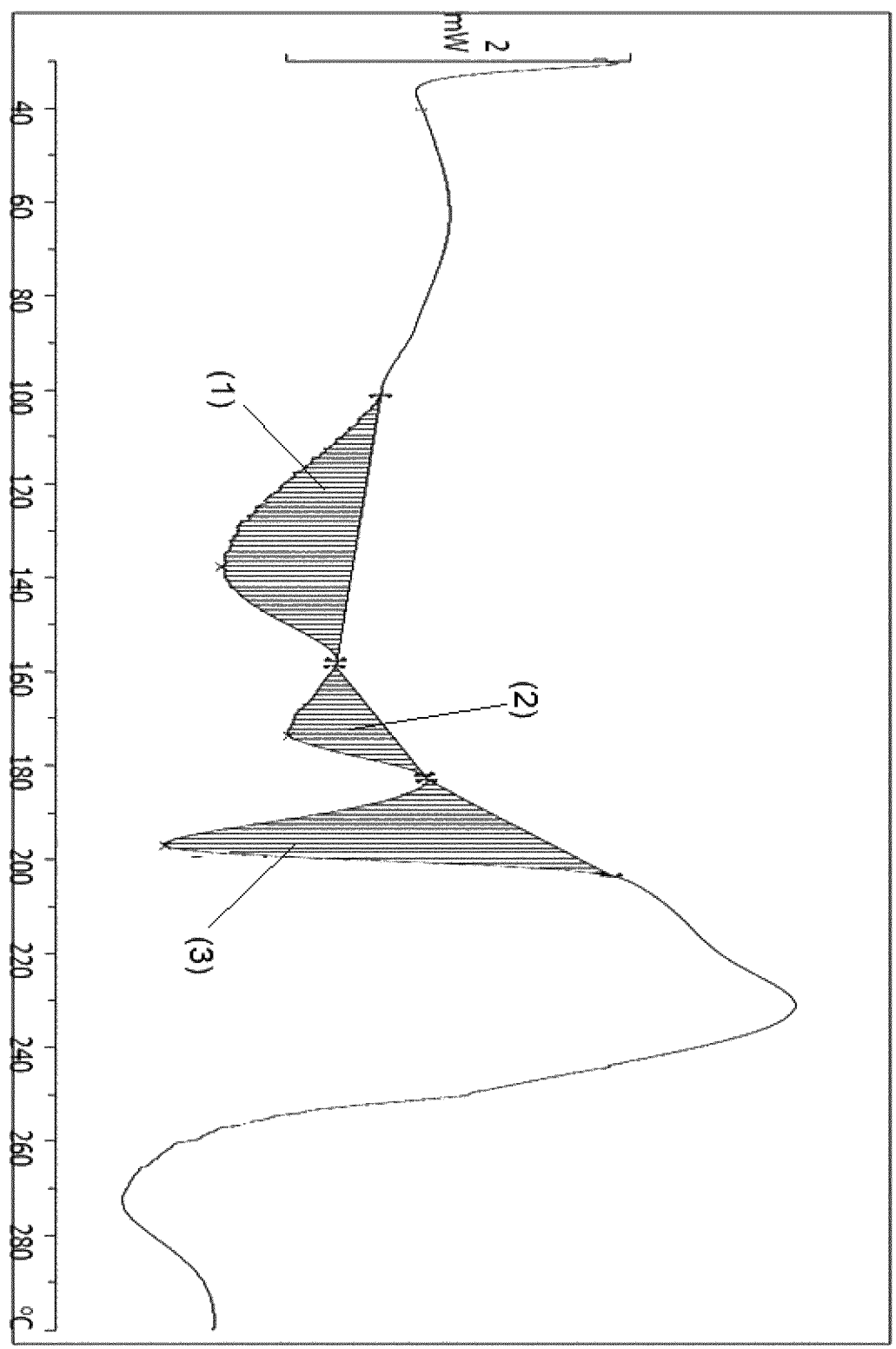
FIG. 5 provides a DSC thermogram of the solvate form $\varepsilon_2$ of eluxadoline.

The solvate form $\varepsilon_2$ is further characterized by:

3. a DSC thermogram showing a feature between 101.1° C. and 157.7° C. (with a maximum at 137.7° C.), an event between 158.8° C. and 182.1° C. (with a maximum at 173.6° C.) and a feature between 182.9° C. and 203.4° C. (with a maximum at 196.9° C.); FIG. 5 shows these different features (1) to (3), wherein (1) has Integral −143.81 mJ, normalized −31.61 Jg$^{-1}$, Onset 136.56° C.; (2) has Integral −43.83 mJ, normalized −9.63 Jg$^{-1}$, Onset 160.37° C.; (3) has Integral −131.78 mJ, normalized −28.96 Jg$^{-1}$, Onset 185.79° C.; and/or 4. a TGA thermogram showing a weight loss step between 25° C. and 135° C. of up to 19.0%.

More preferably solvate form $\varepsilon_3$ shows an X-ray powder diffraction pattern that, when collected with the Kα radiation of copper (λ=1.5418 Å), is characterized by main peaks at:
(viii) 6.36°, 11.000, 12.80°, 18.16° and 23.18°±0.10° 2θ; or
(ix) 6.36°, 9.80°, 11.000, 12.80°, 13.76°, 15.20°, 18.16° and 23.18°±0.10° 2θ.

Even more preferably said solvate form $\varepsilon_3$ shows an X-ray powder diffraction pattern that, when collected with the Kα radiation of copper (λ=1.5418 Å), is characterized by at least 5 peaks (±0.1° 2θ) selected from Table 3A or 3B:

TABLE 3A

| °2θ | d space (Å) | I$_{rel}$ (%) |
| --- | --- | --- |
| 6.36 | 13.8860 | 100 |
| 7.42 | 11.9045 | 17 |
| 9.04 | 9.7745 | 16 |
| 9.80 | 9.0181 | 23 |
| 11.00 | 8.0369 | 23 |
| 12.80 | 6.9104 | 48 |
| 13.76 | 6.4304 | 17 |
| 15.20 | 5.8243 | 18 |
| 15.66 | 15.6542 | 15 |
| 18.16 | 4.8811 | 55 |
| 22.00 | 4.0370 | 17 |
| 23.18 | 3.8341 | 26 |
| 24.14 | 3.6838 | 19 |

TABLE 3B

| °2θ | d space (Å) | I$_{rel}$ (%) |
| --- | --- | --- |
| 6.36 | 13.8860 | 100 |
| 7.42 | 11.9045 | 17 |
| 9.04 | 9.7745 | 16 |
| 9.80 | 9.0181 | 23 |
| 10.42 | 8.4829 | 10 |
| 11.00 | 8.0369 | 23 |
| 12.80 | 6.9104 | 48 |
| 13.76 | 6.4304 | 17 |
| 15.20 | 5.8243 | 18 |
| 15.66 | 5.6542 | 15 |
| 15.96 | 5.5486 | 12 |
| 18.16 | 4.8811 | 55 |
| 18.56 | 4.7768 | 11 |
| 18.90 | 4.6916 | 11 |
| 19.48 | 4.5532 | 11 |
| 20.30 | 4.3711 | 13 |
| 21.22 | 4.1836 | 13 |
| 22.00 | 4.0370 | 17 |
| 23.18 | 3.8341 | 26 |
| 24.14 | 3.6838 | 19 |
| 28.16 | 3.1663 | 11 |

Figure 8:
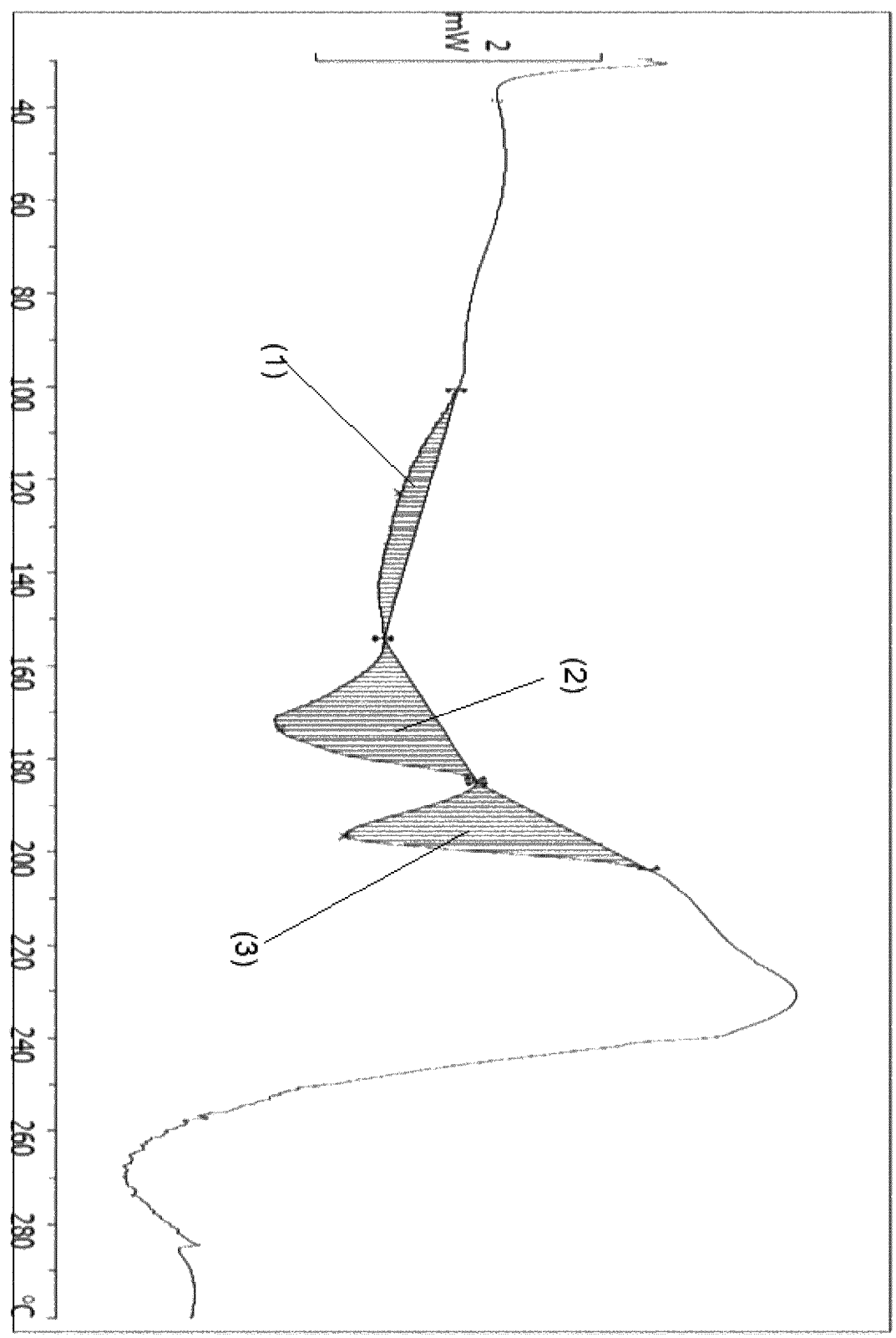
FIG. 8 provides a DSC thermogram of the solvate form $\varepsilon_3$ of eluxadoline.

The solvate form $\varepsilon_3$ is further characterized by:

5. a DSC thermogram showing a feature between 100.7° C. and 154.1° C. (with a maximum at 122.9° C.), an event between 154.1° C. and 184.6° C. (with a maximum at 173.7° C.) and a feature between 185.0° C. and 203.8° C. (with a maximum at 196.6° C.); FIG. 8 shows these different features (1) to (3), wherein (1) has Integral −39.62 mJ, normalized −9.28 Jg$^{-1}$, Onset 104.45° C.; (2) has Integral −105.41 mJ, normalized −24.69 Jg$^{-1}$, Onset 160.27° C.; (3) has Integral −91.70 mJ, normalized −21.47 Jg$^{-1}$, Onset 186.37° C.; and/or 6. a TGA thermogram showing a weight loss step between 25° C. and 145° C. of up to 18.5%.

In a second aspect thereof, the invention refers to a process for the preparation of solvate form ε, or preferably solvate forms $ε_1$, $ε_2$ or $ε_3$ of eluxadoline, said process comprising the steps of:
 a) dispersing eluxadoline and a ketone selected from the group consisting of acetone, 2-butanone, 3-pentanone and mixtures thereof;
 b) maintaining the dispersion under stirring at a temperature from 20° C. to the reflux temperature of the ketone or mixture of ketones used in step a) for at least 30 minutes;
 c) optionally, when step b) has been performed to a temperature higher than 35° C., cooling the mixture to a temperature from 20 to 35° C.; and
 d) recovering the resulting solid and, optionally, drying it.

Eluxadoline suitable to be used in step a) are for example selected from the group comprising, or preferably consisting of, its amorphous form, its polymorphic forms α and β (as disclosed in WO 2009/009480 A2), forms I, II, III, and IV (as disclosed in WO 2017/015606 A1) and its isomorphous solvates forms (as disclosed in EP17382038). The amorphous form of eluxadoline is commercially available, for instance from Dongyang Honsen CO., Ltd. Alternatively, it can be produced starting from a hydrochloride salt of eluxadoline (preferably a dihydrochloride or a monohydrochloride salt thereof) by neutralization with a base and precipitation in water, as described, e.g., in paragraphs [0019] and [0020] of EP 2,176,234 B1 (which are herein incorporated by reference).

Isomorphous solvates forms suitable for the aim are preferably formed using a solvent selected from the group consisting of alcohols; ketones different from acetone, 2-butanone, 3-pentanone, and mixtures thereof; ethers; and a combination of any one of said solvents with water.

More preferably said isomorphous solvates forms are formed using a solvent selected from the group consisting of $C_1$-$C_6$ alcohols (more preferably methanol, ethanol and tert-butanol); ketones different from acetone, 2-butanone, 3-pentanone, and mixtures thereof (more preferably methyl isobutyl ketone); $C_2$-$C_6$ alkyl ethers (more preferably $C_4$-$C_6$ alkyl ethers, even more preferably tetrahydrofuran); and a combination of any one of said solvents with water.

Said isomorphous solvate forms are either stoichiometric (where a definite but not necessary integer ratio of solvent to eluxadoline exists) or non-stoichiometric (where the ratio of solvent to molecule may but not necessarily vary continuously over a given range). While the solvent in stoichiometric solvates is usually an integral part of the crystal structure and is essential for the maintenance of the molecular network in the case of non-stoichiometric solvates, it might be located in certain structural voids and can act mostly as a space filler.

Isomorphous solvates forms suitable to be used in step a) preferably show an XRPD trace with main peaks at 6.20°, 7.28°, 8.92°, 12.68° and 18.08°±0.20° 2θ in a diffractogram collected with the copper Kα radiation (λ=1.5418 Å). More preferably said isomorphous solvates forms show a diffractogram comprising peaks at angles 6.20°, 7.28°, 8.92°, 9.68°, 10.88°, 12.68°, 13.60°, 15.60° and 18.08°±0.20° 2θ in a diffractogram collected with the copper Kα radiation (λ=1.5418 Å). Even more preferably said isomorphous solvates forms show a diffractogram comprising peaks at angles 6.20°, 7.280, 8.92°, 9.680, 10.88°, 12.68°, 13.60°, 15.18°, 15.60°, 15.18°, 18.08°, 19.04°, 22.06° and 23.14°±0.20° 2θ in a diffractogram collected with the copper Kα radiation (λ=1.5418 Å) or an XRPD trace as substantially depicted in FIG. 16.

Figure 16:
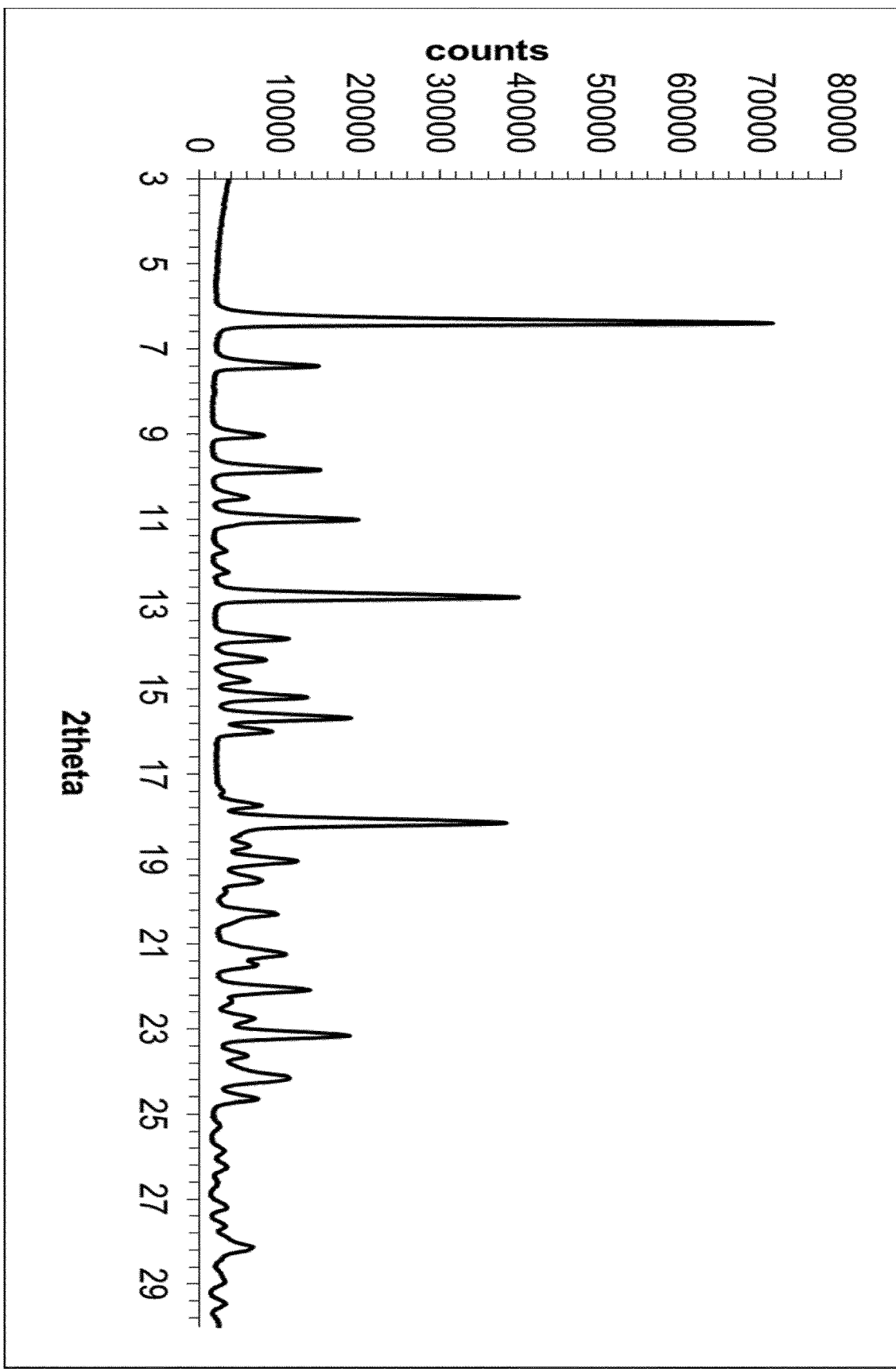
FIG. 16 depicts the X-Ray powder diffractogram of the isomorphous solvate form of eluxadoline.

While not intending to be bound by any theory, it is believed that, said isomorphous solvates forms share the XRPD trace as substantially depicted in FIG. 16 irrespective of:
 the molecule of guest solvent in the crystalline structure;
 the number of solvent species present in the crystalline structure;
 the total amount of any given solvent, be it present alone or in mixture with other solvents.

Isomorphous solvates forms suitable to be used in step a) can be for example prepared by subjecting eluxadoline (either in a solid or in amorphous form) to step d) to h) reported below.

Step a) comprises dispersing eluxadoline, preferably in its amorphous form, in a ketone selected from the group consisting of acetone, 2-butanone, 3-pentanone and mixtures thereof. This step is normally carried out at a temperature from 10° C. to 30° C., preferably from 15° C. to 25° C., even more preferably from 20° C. to 22° C. The amount of ketone can vary in a very wide range; preferably, the overall volume of ketone may vary from 5 mL to 50 mL per gram of eluxadoline; more preferably, the volume is from 7 to 25 mL per gram of eluxadoline; even more preferably from 10 to 15 mL.

According to the following step b), the dispersion resulting from step a) is maintained under stirring at a temperature from 20° C. to the reflux temperature of the ketone or mixture of ketones used in step a) (preferably under reflux conditions) for at least 30 minutes, preferably for a period from 60 minutes to 50 hours, more preferably from 2 hours to 20 hours, even more preferably from 4 to 10 hours.

Optional step c) includes, when step b) has been performed to a temperature higher than 35° C., cooling the mixture to a temperature from 10 to 35° C., preferably from 15° C. to 25° C., even more preferably from 20° C. to 22° C.

Form ε of eluxadoline is recovered in step d) using known techniques such as filtration or centrifugation and optionally dried, e.g. according to the any of the procedures known in the field, preferably by drying the recovered solid at a temperature from 20 to 35° C. (more preferably from 25 to 30° C.) optionally under reduced pressure.

In a third aspect thereof, the invention relates to the use of solvate form ε or, preferably of solvate forms $ε_1$, $ε_2$ or $ε_3$, for producing other polymorphs of eluxadoline.

According to the present invention, "other polymorphs of eluxadoline" or "a crystalline form other than solvate form ε" means any polymorphs of eluxadoline (including its solvate or hydrate forms) available in the art at the date of the present invention. Said polymorphs of eluxadoline may be for example selected from the group comprising, or preferably consisting of, crystalline forms α, β, I, II, III, IV, its amorphous form, its isomorphous solvates forms (as disclosed in EP17382038), and any salts thereof (preferably its monohydrochloride or dihydrochloride salts, as described respectively in EP17382037 and in EP 2,176,234 B1).

According to a preferred embodiment of this aspect of the invention, a process for the preparation of eluxadoline in a crystalline form other than solvate form ε, preferably a process for the preparation of eluxadoline in an isomorphous solvate form, is provided, said process comprising:
 e) dispersing the solvate form ε or, preferably solvate forms $ε_1$, $ε_2$ or $ε_3$, in at least one solvent;

f) maintaining the dispersion to a temperature from 25° C. to the reflux temperature of the at least one solvent used in step d) for at least 30 minutes;

g) optionally, when step e) has been performed to a temperature higher than 35° C., cooling the mixture to a temperature from 20 to 35° C.; and h) recovering the resulting solid and, optionally, drying it; with the proviso that the at least one solvent used in step e) is not acetone, 2-butanone or 3-pentanone.

Step e) comprises dispersing the solvate form ε of eluxadoline, preferably the solvate forms $\epsilon_1$, $\epsilon_2$ or $\epsilon_3$, in at least one solvent with the proviso that said at least one solvent is not acetone, 2-butanone or 3-pentanone. This step is normally carried out at a temperature from 10° C. to 30° C., preferably from 15° C. to 25° C., even more preferably from 20° C. to 22° C. Preferably, the at least one solvent used in step e) is selected from the group consisting of ethanol, 2-propanol, tert-butanol, tetrahydrofuran and a mixture of any of these solvents with water, more preferably 2-propanol or a mixture thereof with water. The amount of solvent can vary in a very wide range; preferably, the overall volume of ketone may vary from 5 mL to 50 mL per gram of eluxadoline; more preferably, the volume is from 7 to 25 mL per gram of eluxadoline; even more preferably from 10 to 15 mL.

According to the following step f), the dispersion resulting from step e) is maintained at a temperature from 25° C. to the reflux temperature of the at least one solvent used in step e) (preferably under reflux conditions) for at least 30 minutes, preferably for a period from 60 minutes to 50 hours, more preferably from 2 hours to 20 hours, even more preferably from 4 to 10 hours.

Optional step g) includes, when step f) has been performed to a temperature higher than 35° C., cooling the mixture to a temperature from 10 to 35° C., preferably from 15° C. to 25° C., even more preferably from 20° C. to 22° C.

The crystalline form other than solvate form c, preferably an isomorphous solvate form of eluxadoline, is recovered in step h) using known techniques such as filtration or centrifugation and optionally dried, e.g. according to the any of the procedures known in the field, preferably by treating the recovered solid at a temperature from 20 to 35° C. (more preferably from 25 to 30° C.) optionally under reduced pressure.

A preferred embodiment of this aspect of the invention relates to a process for preparing a crystalline form α' of eluxadoline which is polymorphically and chemically stable, said process comprising heating the solvate form of c eluxadoline, or preferably the solvate forms $\epsilon_1$, $\epsilon_2$ or $\epsilon_3$, to a temperature from 20° C. to 60° C., preferably from 25° C. to 45° C., even more preferably from 30° C. to 40° C., optionally under reduced pressure for a period from 5 to 50 hours, preferably from 10 to 25 hours, even more preferably from 15 to 20 hours. Therefore, the present invention also provides a novel crystalline form α' of eluxadoline obtainable starting from the solvate form of c eluxadoline.

According to another embodiment thereof, the present invention provides for a polymorphically and chemically stable crystalline form α' of eluxadoline. Said polymorphically and chemically stable crystalline form α' of eluxadoline can be further characterized by at least one of the following features:

(x). an X-ray powder diffraction pattern that, when collected with the Kα radiation of copper (λ=1.5418 Å), is characterized by main peaks at: 7.98°, 13.94°, 14.28°, 14.66°, and 19.04° 2θ±0.1° 2θ; and/or (xi). an X-ray powder diffraction pattern that, when collected with the Kα radiation of copper (λ=1.5418 Å), is characterized by main peaks at: 7.98°, 11.26°, 13.94°, 14.28°, 14.66°, 17.08°, 19.04° and 21.56° 2θ±0.1° 2θ; and/or (xii). a DSC thermogram showing, when performed with a heating ramp of 10° C./min, a feature between 163.7° C. and 214.8° C. (with a maximum at 198.9° C.) (2);

(xiii) a DSC thermogram showing, when performed with a heating ramp of 10° C./min, a feature between 40.2° C. and 82.7° C. (with a maximum at 61.2° C.) (1) and an event between 163.7° C. and 214.8° C. (with a maximum at 198.9° C.) (2).

Figure 12:
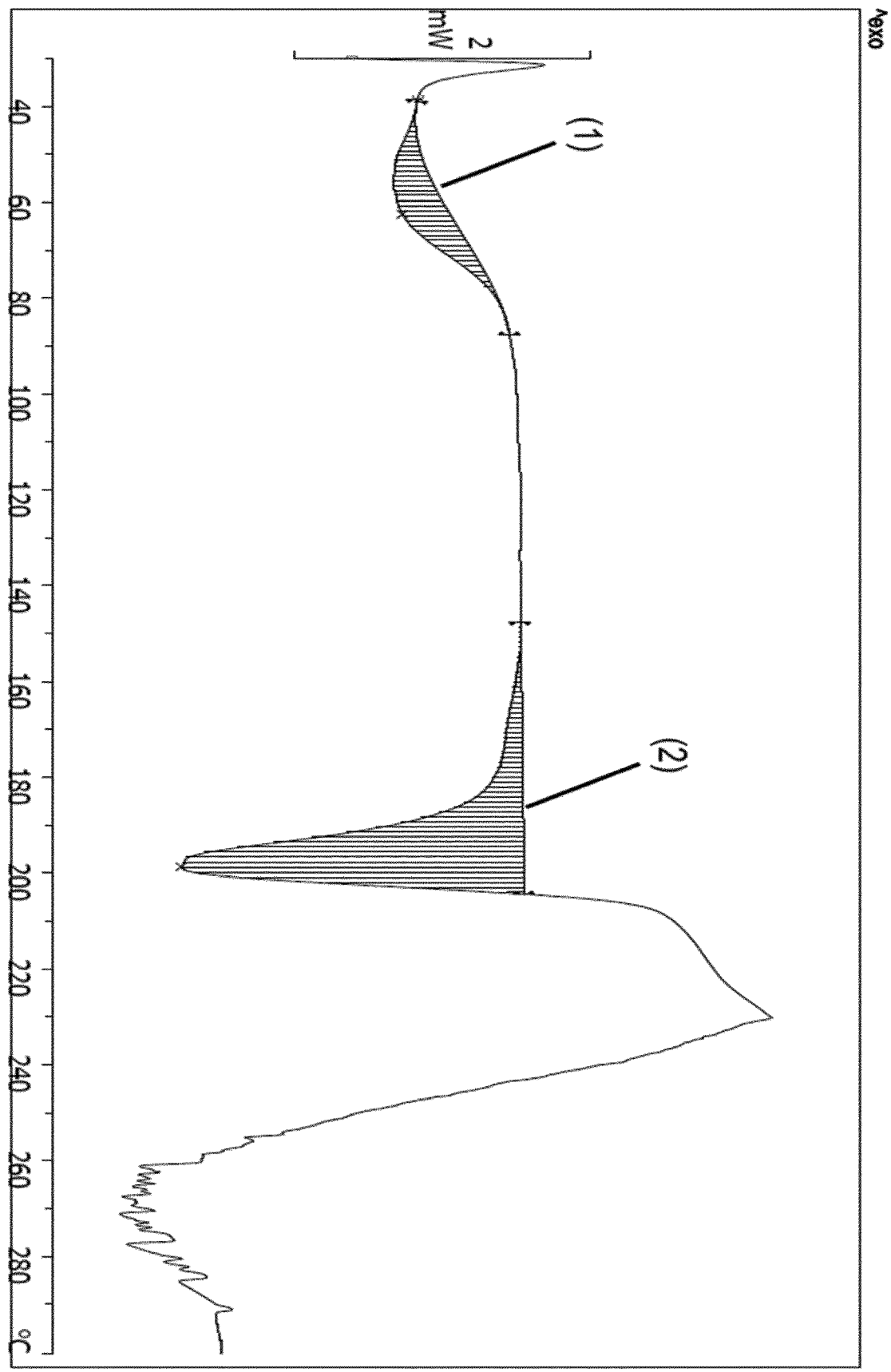
FIG. 12 provides a DSC thermogram of the polymorphically and chemically stable form α' of eluxadoline.
Figure 13:
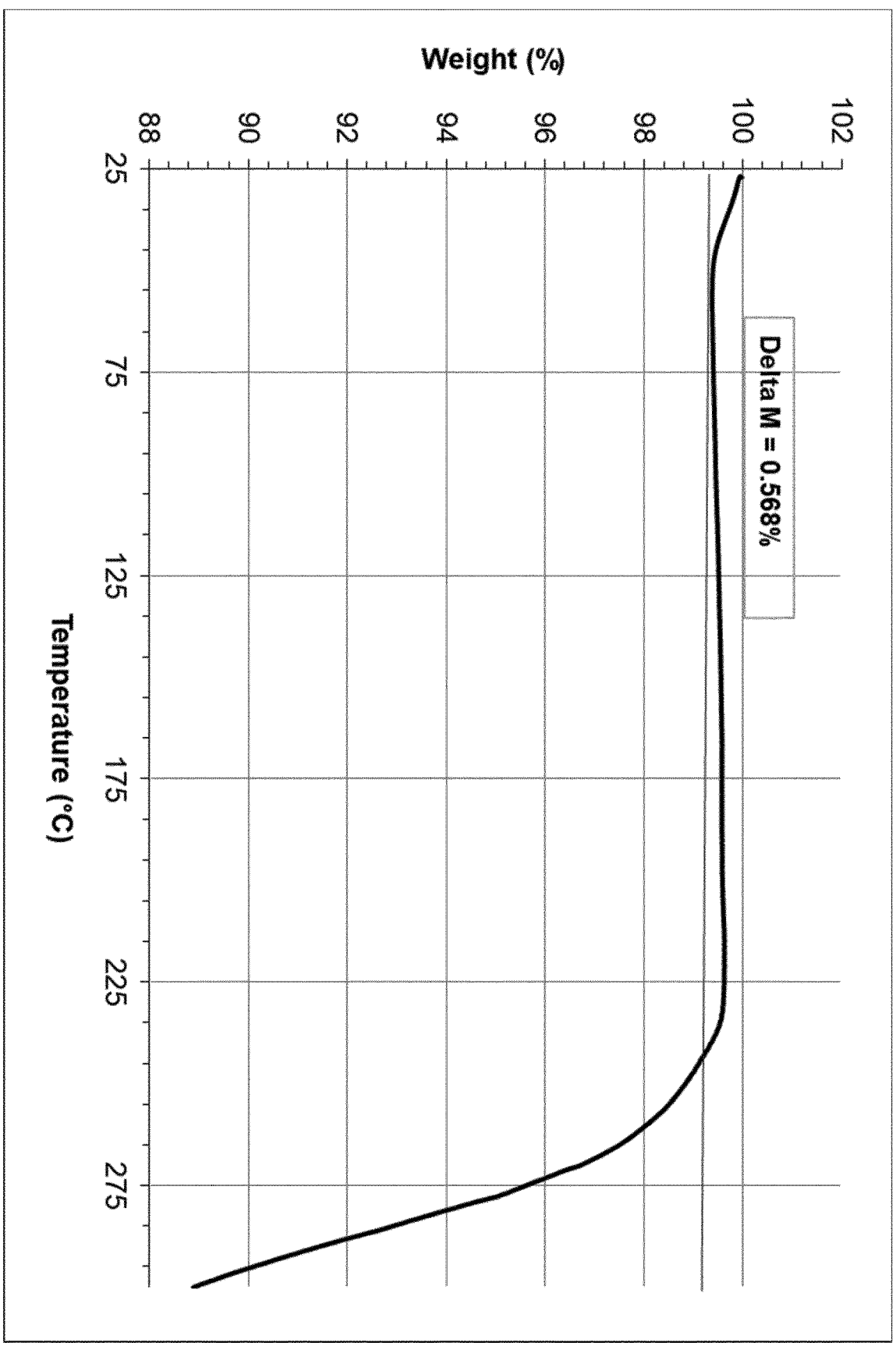
FIG. 13 provides a TGA thermogram of the polymorphically and chemically stable form α' of eluxadoline.

FIG. 12 shows these features (1) and (2), wherein (1) has Integral −55.79 mJ, normalized −15.00 Jg$^{-1}$, Onset 41.38° C.; (2) has Integral −247.26 mJ, normalized −66.47 Jg$^{-1}$, Onset 185.89° C.; and/or (xiv). a TGA thermogram showing a weight loss step between 25° C. and 80° C. of up to 1%, and preferably of up to 0.7%; and/or (xv). SEM images as substantially depicted in any one of FIG. 15; and/or (xvi). a particle size distribution with a span of less than 2.5, preferably below 1.8 and more preferably below 1.5; and/or (xvii). a melting point from 189 to 191° C.; and/or (xviii). a DVS isotherm as substantially depicted in FIG. 14; and/or (xix). chemical stability when exposed to a temperature of 120° C. for 24 hours, as determined by the content of the impurity at relative retention time of 1.11 below 0.50 A %, preferably below 0.40 A %, more preferably below 0.30 A %, even more preferably of at maximum 0.20 A %;

(xx) chemical stability when exposed to a temperature of 120° C. for 48 hours, as determined by the content of the impurity at relative retention time of 1.11 below 0.50 A %, preferably below 0.40 A %, more preferably below 0.30 A %, even more preferably of at maximum 0.20 A %; and (xxi) a combination of any two or more (x)-(xx);
wherein the relative retention time under items (xix) and (xx) is determined according to the conditions included below in HPLC-UV method.

More preferably the polymorphically and chemically stable crystalline form α' of eluxadoline shows an X-ray powder diffraction pattern that, when collected with the Kα radiation of copper (λ=1.5418 Å), is characterized by at least 5 peaks (±0.1° 2θ) selected from Table 4A or 4B:

TABLE 4A

| °2θ | d space (Å) | $I_{rel}$ (%) |
|---|---|---|
| 7.98 | 11.0703 | 100 |
| 11.26 | 7.8519 | 32 |
| 11.74 | 7.5319 | 29 |
| 13.94 | 6.3478 | 40 |
| 14.28 | 6.1974 | 56 |
| 14.66 | 6.0376 | 57 |
| 17.08 | 5.1872 | 39 |
| 18.08 | 4.9025 | 20 |
| 18.26 | 4.8546 | 22 |
| 19.04 | 4.6574 | 40 |
| 20.08 | 4.4185 | 29 |
| 21.56 | 4.1184 | 30 |
| 22.76 | 3.9039 | 21 |
| 23.70 | 3.7511 | 23 |

TABLE 4B

| °2θ | d space (Å) | $I_{rel}$ (%) |
|---|---|---|
| 7.28 | 12.1331 | 12 |
| 7.98 | 11.0703 | 100 |
| 9.32 | 9.4814 | 13 |
| 10.20 | 8.6653 | 17 |
| 11.26 | 7.8519 | 32 |
| 11.74 | 7.5319 | 29 |
| 13.10 | 6.7528 | 11 |
| 13.94 | 6.3478 | 40 |
| 14.28 | 6.1974 | 56 |
| 14.66 | 6.0376 | 57 |
| 15.68 | 5.6470 | 18 |
| 16.06 | 5.5143 | 18 |
| 16.70 | 5.3044 | 17 |
| 17.08 | 5.1872 | 39 |
| 18.08 | 4.9025 | 20 |
| 18.26 | 4.8546 | 22 |
| 18.48 | 4.7973 | 16 |
| 18.70 | 4.7413 | 15 |
| 19.04 | 4.6574 | 40 |
| 20.08 | 4.4185 | 29 |
| 21.56 | 4.1184 | 30 |
| 22.48 | 3.9519 | 15 |
| 22.76 | 3.9039 | 21 |
| 23.70 | 3.7511 | 23 |
| 24.38 | 3.6480 | 16 |
| 24.98 | 3.5618 | 18 |
| 25.76 | 3.4556 | 17 |
| 27.86 | 3.1998 | 10 |

Even more preferably said polymorphically and chemically stable crystalline form α' of eluxadoline is obtainable by the process described above which comprises heating the solvate form c of eluxadoline, or preferably the solvate forms $\varepsilon_1$, $\varepsilon_2$ or $\varepsilon_3$, to a temperature from 20° C. to 60° C., preferably from 25° C. to 45° C., even more preferably from 30° C. to 40° C., optionally under reduced pressure for a period from 5 to 50 hours, preferably from 10 to 25 hours, even more preferably from 15 to 20 hours.

According to further embodiment of the invention, a process for the preparation of the crystalline form α of eluxadoline, preferably a process for the preparation of the crystalline form α' of eluxadoline, is provided, said process comprising:

i) dispersing the amorphous form of eluxadoline in a mixture comprising at least one organic solvent and water;

j) maintaining the dispersion to a temperature from 25° C. to the reflux temperature of the solvent mixture used in step i) for at least 20 minutes;

k) optionally, when step j) has been performed to a temperature higher than 35° C., cooling the mixture to a temperature from 20 to 35° C.; and l) recovering the resulting solid and, optionally, drying it.

Step i) comprises dispersing the amorphous form of eluxadoline, in a mixture comprising at least one organic solvent (preferably an acetate, more preferably ethyl acetate) and water. This step is normally carried out at a temperature from 10° C. to 30° C., preferably from 15° C. to 25° C., even more preferably from 20° C. to 22° C. The amount of solvent can vary in a very wide range; preferably, the overall volume of the mixture comprising the at least one organic solvent may vary from 5 mL to 50 mL per gram of eluxadoline; more preferably, the volume is from 7 to 25 mL per gram of eluxadoline; even more preferably from 10 to 15 mL.

The ratio between the at least one organic solvent and water in said mixtures can vary in a very wide range; preferably from 0.5:1 to 10:1 (V/V), more preferably from 0.7:1 to 10:1 (V/V), even more preferably from 1:1 to 4:1 (V/V).

According to the following step j), the dispersion resulting from step i) is maintained at a temperature from 25° C. to the reflux temperature of the mixture used in step i) (preferably under reflux conditions) for at least 20 minutes, preferably for a period from 1 hour to 30 hours, more preferably from 3 hours to 20 hours.

Optional step k) includes, when step j) has been performed to a temperature higher than 35° C., cooling the mixture to a temperature from 10 to 35° C., preferably from 15° C. to 25° C., even more preferably from 20° C. to 22° C.

The crystalline form α of eluxadoline, preferably its crystalline form α', is recovered in step l) using known techniques such as filtration or centrifugation and optionally dried, e.g. according to the any of the procedures known in the field, preferably by treating the recovered solid at a temperature from 20° C. to 60° C. (preferably from 25° C. to 45° C., more preferably from 30° C. to 40° C.) optionally under reduced pressure.

In a possible variant of this embodiment, an optional step k') is carried out between steps k) and l), comprising maintaining under stirring the mixture resulting from step k) for at least 30 minutes, preferably for a period from 1 hour to 30 hours, more preferably from 3 hours to 20 hours.

The crystalline form α and the crystalline form α' as obtainable by the process comprising steps i) to l) represent a further embodiment of the present invention.

The invention will be further illustrated by the following examples.

The instruments and methods used to characterize the crystalline forms obtained in the examples are as follows:

XRPD:

Analyses were performed on a Bruker AXS D8 Advance diffractometer (40 kV, 40 mA, λ=1.5418 Å), equipped with a linear Lynxeye position sensitive detector, set at 300 mm from the sample (Ni-filtered Cu-K$\alpha_{1,2}$ radiation). Data collection was made in coupled mode and in theta-theta configuration, in the 3-30° 2-theta, sampling with a 0.02° step scan. Samples were gently ground in an agate mortar, and then deposited in the 0.2 mm-deep hollow of a silicon monocrystal zero background plate.

Unit cell parameters were obtained through the use of standard Peak Hunting procedures, followed by Profile Fitting and ab-initio Indexing, through the Singular-Value Decomposition approach developed by A. A. Coelho (*Journal of Applied Crystallography*, 2003, 36, 86). These approximate lattice parameters were then refined by the structureless Le Bail method (*Powder Diffraction*, 2005, 20, 316) using the TOPAS-R suite of programs (V. 3.0, 2005, Bruker AXS, Karlsruhe, Germany).

NMR:

$^1$H NMR solution spectra were performed on a Jeol Eclipse 300 at 298 K, using DMSO-$d_6$ as solvent. Chemical shifts are measured in δ ppm relative to tetramethylsilane. Accurately weighted amounts of sample were dissolved in a suitable test NMR tube and analysed with 10 seconds delay.

DSC:

DSC tests were conducted by use of a Mettler-Toledo DSC1 Stare System. Indium was used for calibration. Accurately weighed samples (3-5 mg) were placed in open aluminum vented pans and heated at a rate of 10° C./min under 80 mL/min nitrogen purge. Range from 30° C. up to 300° C. was investigated.

TGA:

TGA analyses were performed by means of a Perkin-Elmer Pyris 1 TGA instrument endowed with an EGA oven and a platinum sampler. The samples (approximately 6-7 mg) were heated with a scan rate of 10° C./min under a 90 mL/min nitrogen purge from 25 to 700° C. The instrument was calibrated with calcium oxalate di-hydrate.

Dissolution Test:

Dissolution tests were performed by means of Sotax AT7 Smart equipped with 6×800 mL volume vessels and using a 50 mM phosphate buffer pH=7.4, previously heated to 37° C. 20 mg of the sample to be tested were placed in each vessel, and stirred (with paddles) at 110 rpm for 60 minutes at 37±0.2° C. Aliquots were taken at 5, 10, 20, 30, 45 and 60 min, filtered through 0.45 μm Chromafil Xtra RC 45/25 syringe filter and analysed by UV/VIS spectrometer Perkin Elmer Lambda 35, 1 cm quartz cell (absorbance at 203 nm). pH was determined using a Mettler Toledo pH Meter FE20 equipped with a InLab®420 electrode.

SEM Method:

Samples in powder were deposited on a carbon tab fixed on an aluminium stub. Samples were scanned on FE-SEM working in high vacuum Zeiss Supra 40 equipped with the GEMINI column. The microscope is also equipped with a microanalysis apparatus for EDS elemental analysis (Oxford Instruments). Conditions EHT 10 kV with Everhart-Thornley Secondary Electron Detector.

Melting Point:

Tests performed by means of a M-560 Buchi instrument. Set point: 180° C.; scan: 2° C./min.

Particle Size Distribution:

The distribution of eluxadoline particles of the present invention was determined by laser scattering using, in particular, a laser beam diffraction instrument Malvern® Mastersizer 2000 (Malvern Instruments Ltd., Worcestershire, UK). Samples of eluxadoline were suspended in isopar G, then sonicated for 180 seconds to completely disperse the particles. The dispersion was circulated in the flow cell of Malvern® Mastersizer 2000 until a stable signal is obtained (normally 60 seconds) before the measurement.

High Performance Liquid Chromatography-Ultraviolet Detection (HPLC-UV):

Chemical stability tests were performed using the following HPLC method

Column: XBridge C8 150×4.6 mm, 3.5 μm

Mobile Phase A: 0.1% (V/V) phosphoric acid aqueous solution

Mobile Phase B: Acetonitrile

Diluent: 1:1 (V/V) Mixture of Mobile Phases A and B

Flow Rate: 1.3 mL/min

Runtime: 35 min

Column Temperature 30° C.

Autosampler Temperature: Ambient

Injection Volume: 5 μL

Detection: 210 nm

Sample concentration: 0.4 mg/mL

Gradient Program:

| Time (min.) | A (%) | B (%) |
|---|---|---|
| 0 | 95 | 5 |
| 35 | 60 | 40 |
| 36 | 10 | 90 |
| 40 | 10 | 90 |
| 41 | 95 | 5 |
| 55 | 95 | 5 |

Example 1

Preparation of Solvate Form $\varepsilon_1$ of Eluxadoline.

One gram of eluxadoline in amorphous form was suspended in 10 mL of acetone at 20-25° C. in a glass flask equipped with a magnetic stirrer thermometer, magnetic stirrer and condenser. The resulting suspension was heated under stirring to the reflux temperature (about 55° C.), maintained under stirring at the same temperature for 8 hours and then cooled to 20-25° C. The solid was filtered, thus affording crystalline form $\varepsilon_1$ of eluxadoline as a white solid.

The obtained product was analysed by XRPD, obtaining the diffractogram shown in FIG. 1.

A $^1$H NMR analysis of a portion of the product confirmed the formation of the desired solvate form.

Figure 3:
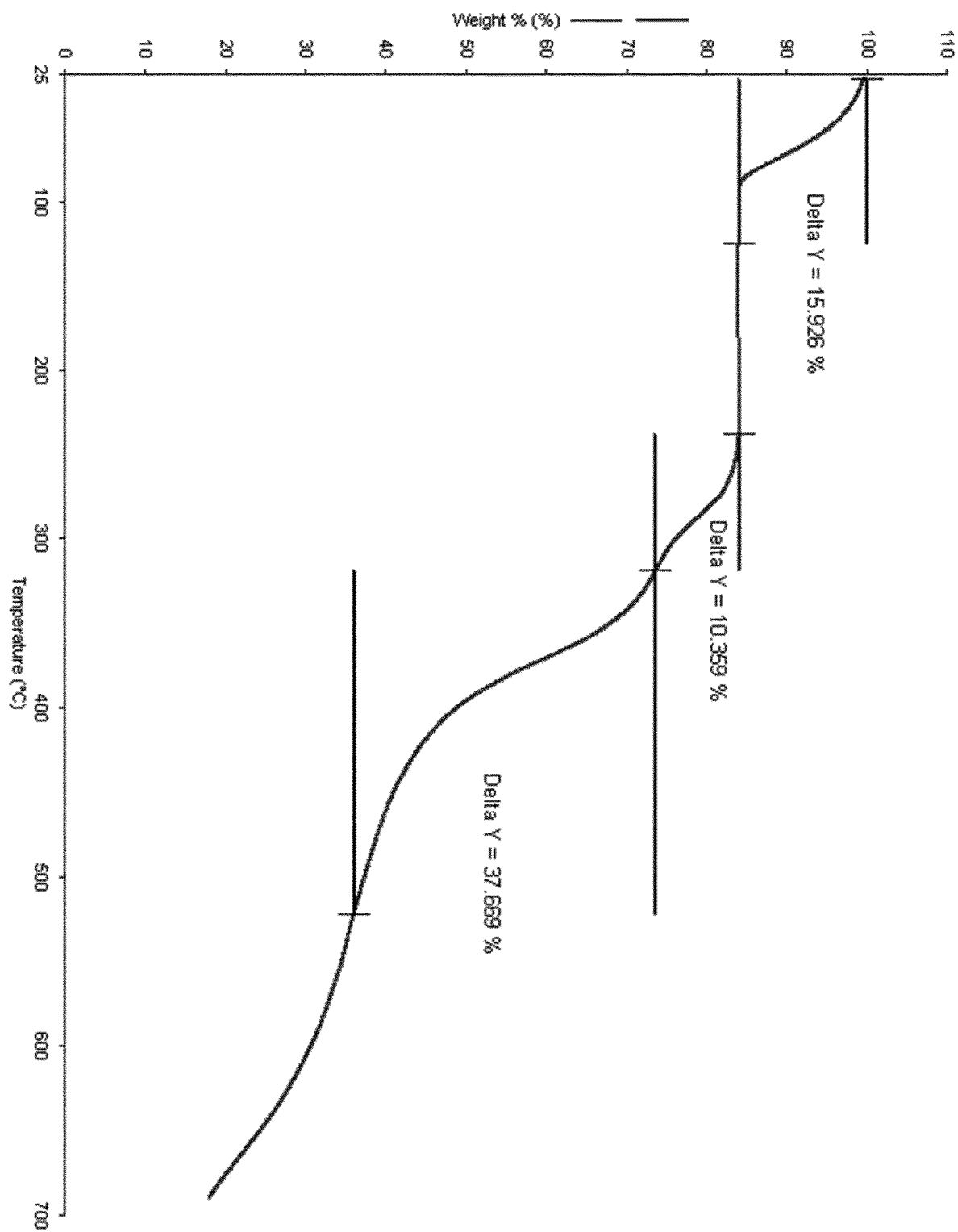
FIG. 3 provides a TGA thermogram of the solvate form $\varepsilon_1$ of eluxadoline.

The product was also subjected to DSC and TGA analyses, which gave as result the graphs shown in FIGS. 2 and 3.

Example 2

Preparation of Solvate Form $\varepsilon_2$ of Eluxadoline.

One gram of eluxadoline in amorphous form was suspended in 10 mL of 2-butanone at 20-25° C. in a glass flask equipped with a magnetic stirrer thermometer, magnetic stirrer and condenser. The resulting suspension was heated under stirring to the reflux temperature (about 80° C.), maintained under stirring at the same temperature for 10 hours and then cooled to 20-25° C. The solid was filtered, thus affording crystalline form $\varepsilon_2$ of eluxadoline as a white solid.

Figure 4:
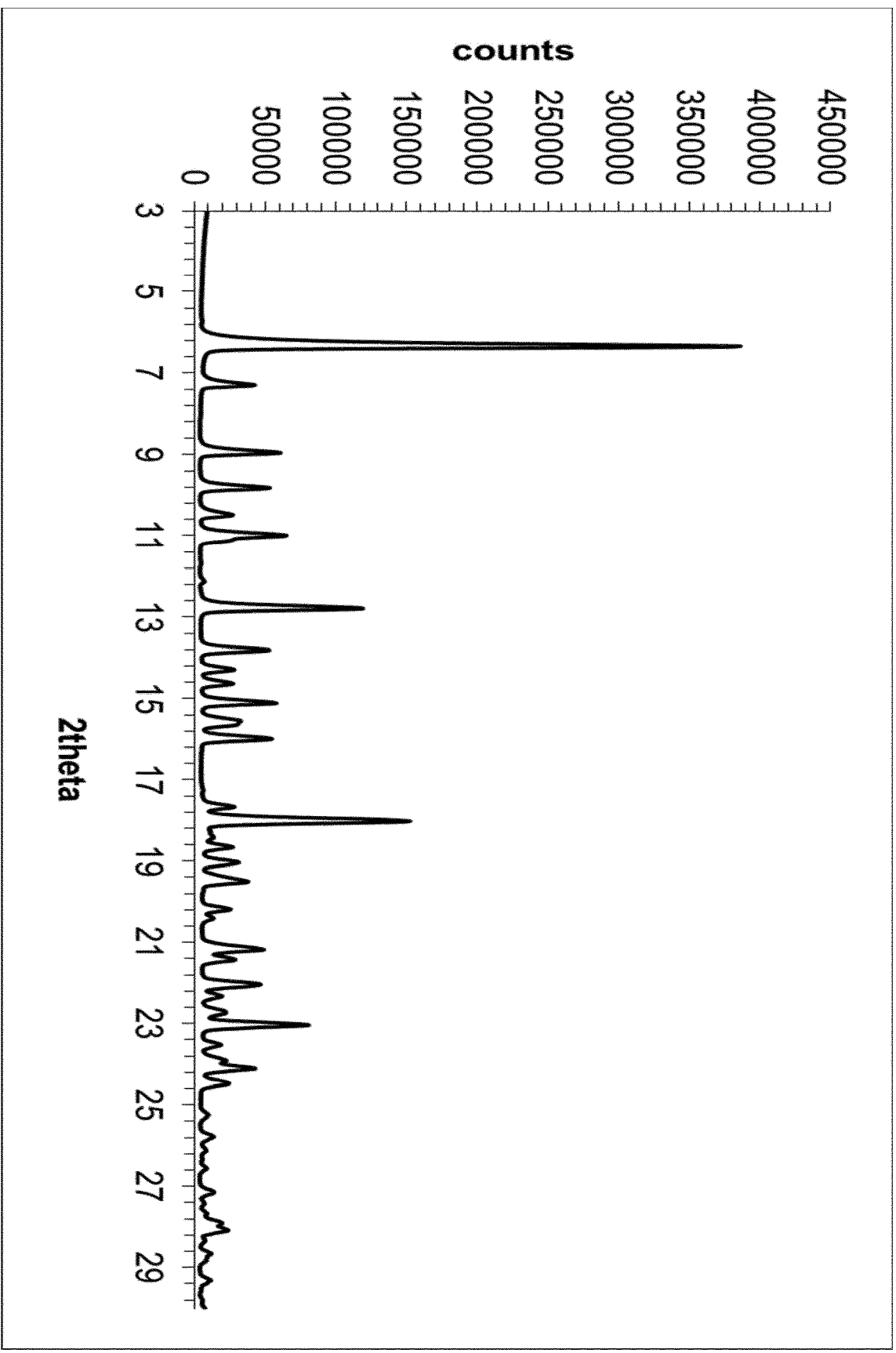
FIG. 4 depicts the X-Ray powder diffractogram of the solvate form $\varepsilon_2$ of eluxadoline.

The obtained product was analysed by XRPD, obtaining the diffractogram shown in FIG. 4.

A $^1$H NMR analysis of a portion of the product confirmed the formation of the desired solvate form.

Figure 6:
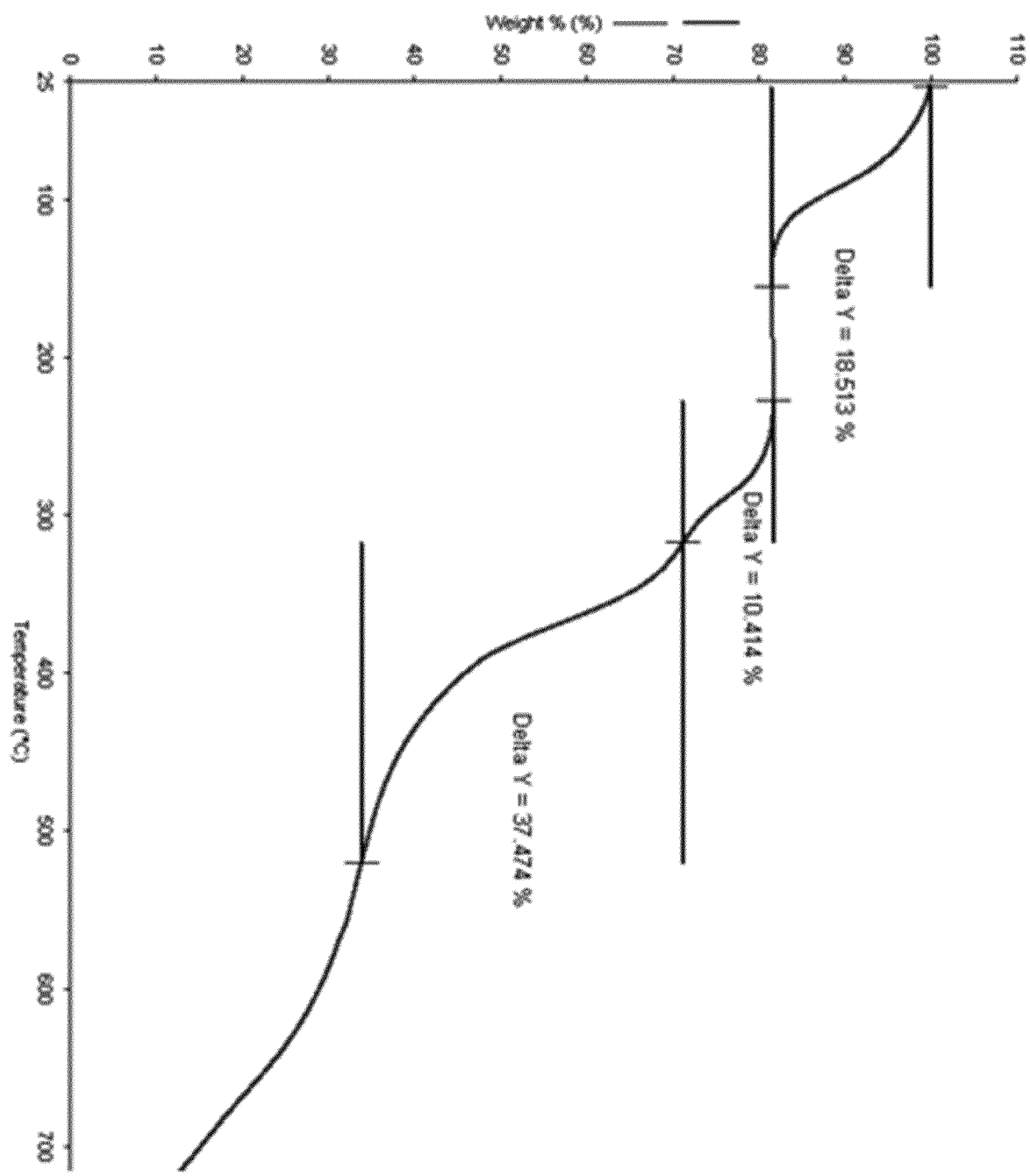
FIG. 6 provides a TGA thermogram of the solvate form $\varepsilon_2$ of eluxadoline.

The product was also subjected to DSC and TGA analyses, which gave as result the graphs shown in FIGS. 5 and 6.

Example 3

Preparation of Solvate Form $\varepsilon_3$ of Eluxadoline.

One gram of eluxadoline in amorphous form was suspended in 10 mL of 3-pentanone at 20-25° C. in a glass flask equipped with a magnetic stirrer thermometer, magnetic stirrer and condenser. The resulting suspension was heated under stirring to the reflux temperature (about 100° C.), maintained under stirring at the same temperature for 10 hours and then cooled to 20-25° C. The solid was filtered, thus affording crystalline form $\varepsilon_3$ of eluxadoline as a white solid.

Figure 7:
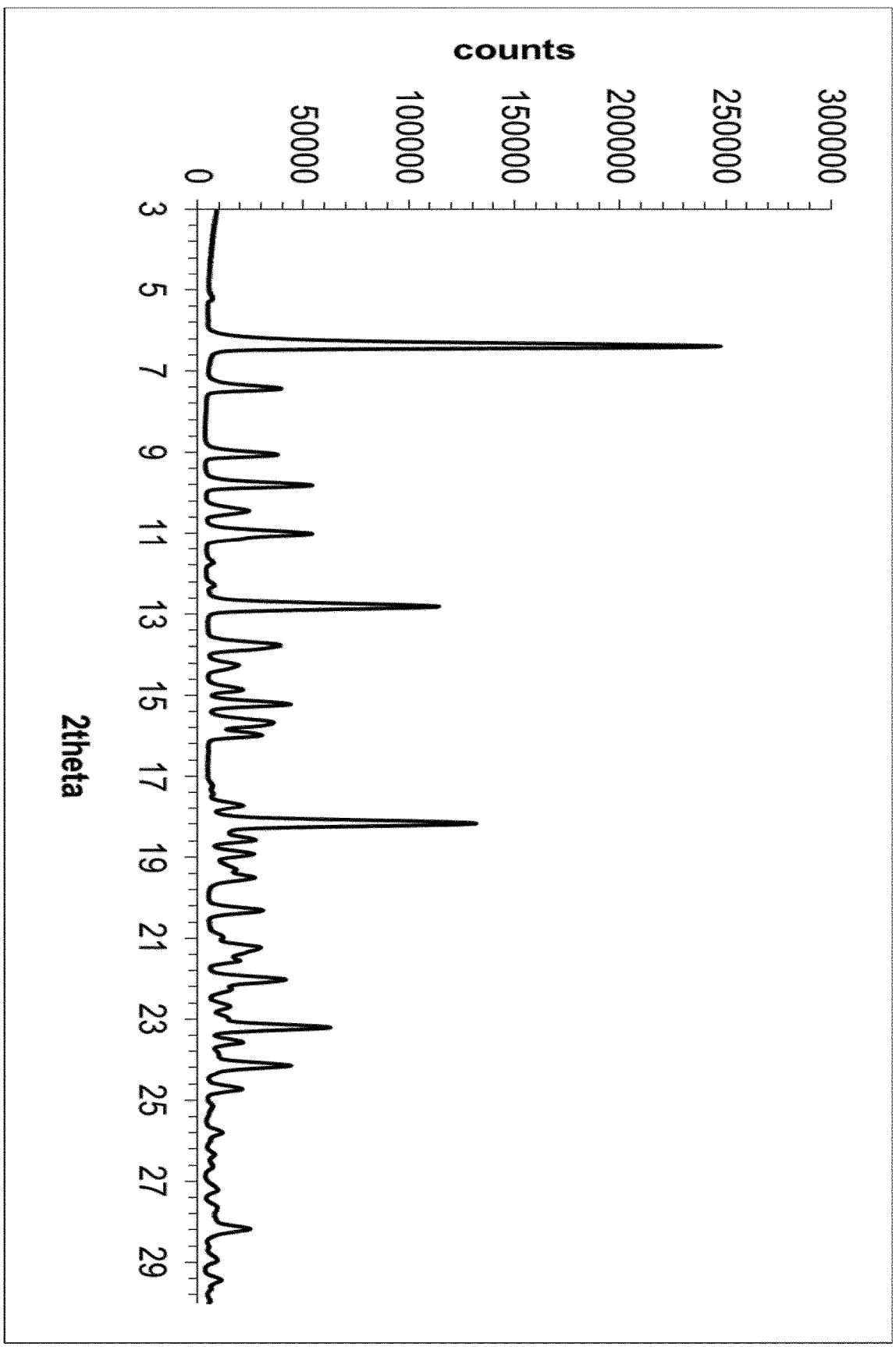
FIG. 7 depicts the X-Ray powder diffractogram of the solvate form $\varepsilon_3$ of eluxadoline.

The obtained product was analysed by XRPD, obtaining the diffractogram shown in FIG. 7.

A $^1$H NMR analysis of a portion of the product confirmed the formation of the desired solvate form.

Figure 9:
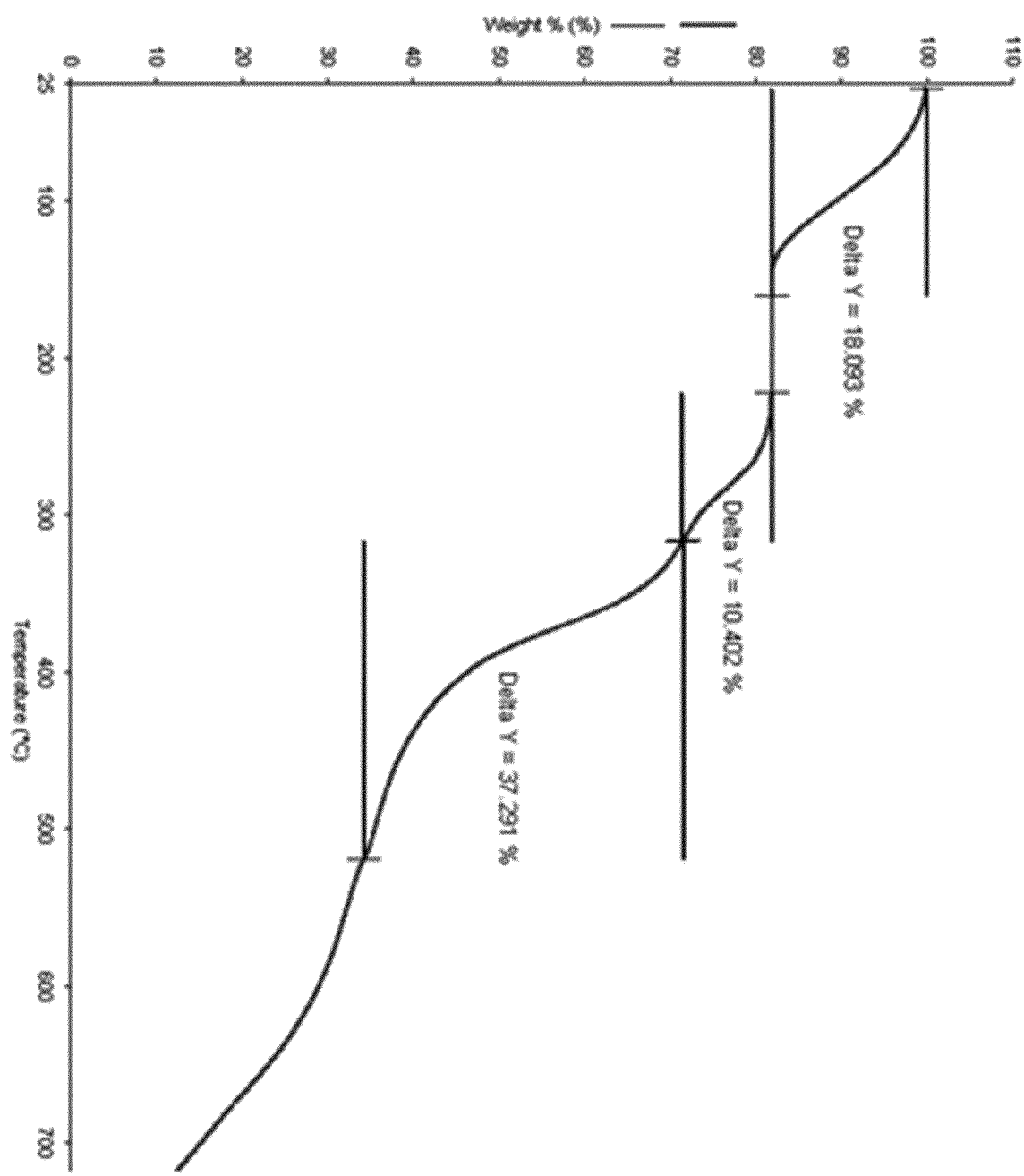
FIG. 9 provides a TGA thermogram of the solvate form $\varepsilon_3$ of eluxadoline.

The product was also subjected to DSC and TGA analyses, which gave as result the graphs shown in FIGS. 8 and 9.

Example 4

Preparation of Solvate Form $\varepsilon_1$ of Eluxadoline.

One gram of eluxadoline in amorphous form was suspended in 10 mL of acetone at 20-25° C. in a glass flask equipped with a magnetic stirrer thermometer, magnetic stirrer and condenser. The resulting suspension was maintained under stirring at the same temperature for 16 hours. The solid was filtered, thus affording crystalline form $\varepsilon_1$ of eluxadoline as a white solid.

The product is characterized by XRPD, DSC and TGA spectra corresponding to those obtained in example 1.

Example 5

Preparation of Solvate Form $\varepsilon_2$ of Eluxadoline.

One gram of eluxadoline in amorphous form was suspended in 10 mL of 2-butanone at 20-25° C. in a glass flask equipped with a magnetic stirrer thermometer, magnetic stirrer and condenser. The resulting suspension was maintained under stirring at the same temperature for 16 hours. The solid was filtered, thus affording crystalline form $\varepsilon_2$ of eluxadoline as a white solid.

The product is characterized by XRPD, DSC and TGA spectra corresponding to those obtained in example 2.

Example 6

Preparation of Solvate Form $\varepsilon_3$ of Eluxadoline.

One gram of eluxadoline in amorphous form was suspended in 10 mL of 3-pentanone at 20-25° C. in a glass flask equipped with a magnetic stirrer thermometer, magnetic stirrer and condenser. The resulting suspension was maintained under stirring at the same temperature for 16 hours. The solid was filtered, thus affording crystalline form $\varepsilon_3$ of eluxadoline as a white solid.

The product is characterized by XRPD, DSC and TGA spectra corresponding to those obtained in example 3.

Example 7

Preparation of Amorphous Form of Eluxadoline.

One gram of eluxadoline in amorphous form was dissolved in 10 mL of cyclohexanone at 80-85° C. in a glass flask equipped with a magnetic stirrer thermometer, magnetic stirrer and condenser. The resulting solution was maintained under stirring at the same temperature for 1 hour then cooled to 20-25° C. The solid was filtered, thus affording amorphous form of eluxadoline as a yellow solid.

Example 8

Preparation of Eluxadoline Cyclohexanone Solvate.

One gram of eluxadoline in amorphous form was suspended in 10 mL of cyclohexanone at 20-25° C. in a glass flask equipped with a magnetic stirrer thermometer, magnetic stirrer and condenser. The resulting suspension was maintained under stirring at the same temperature for 48 hours. The solid was filtered, thus affording eluxadoline cyclohexanone solvate as confirmed by $^1$H NMR analysis.

Figure 10:
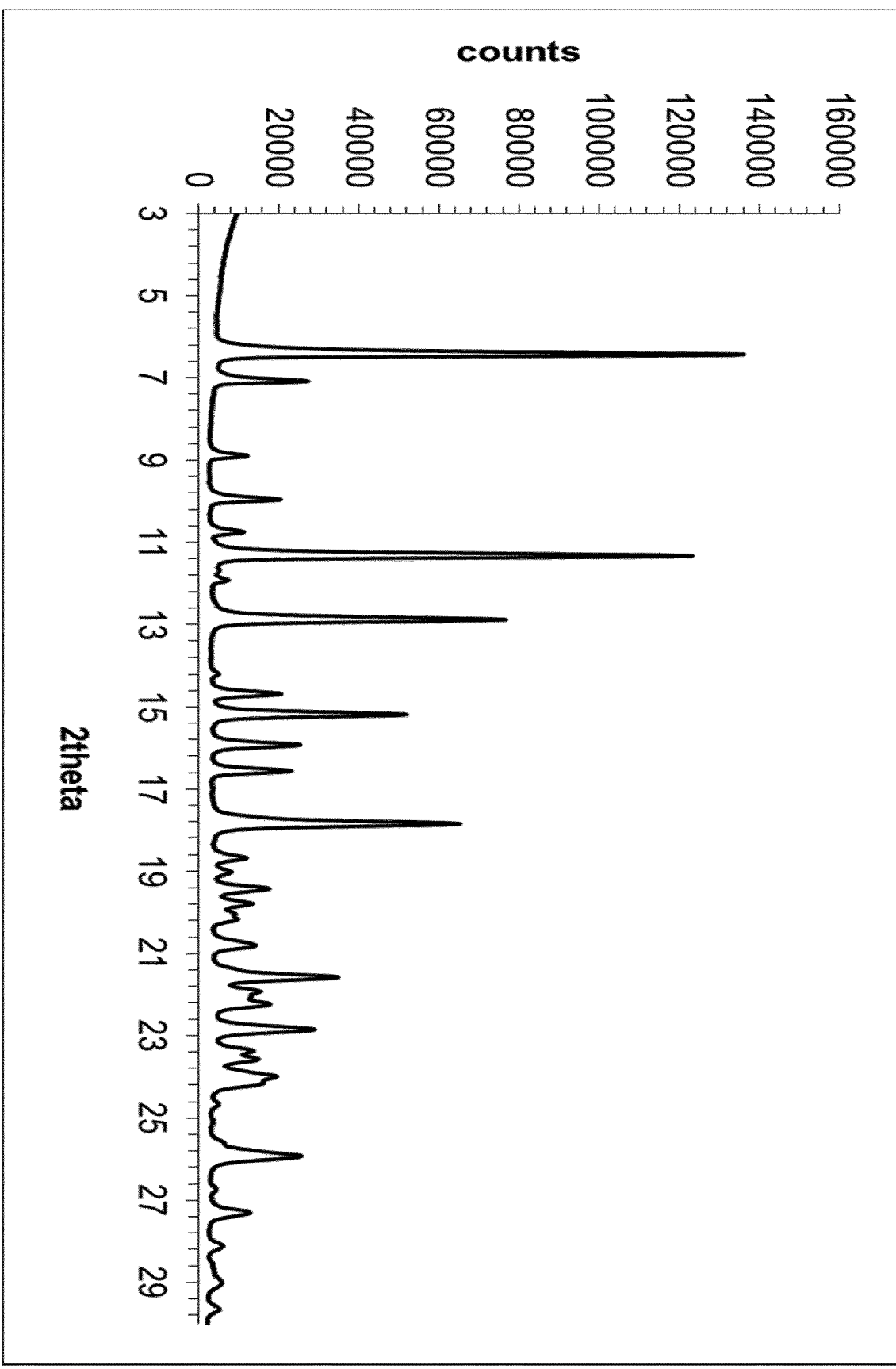
FIG. 10 depicts the X-Ray powder diffractogram of eluxadoline cyclohexanone solvate.

The obtained product was analysed by XRPD, obtaining the diffractogram shown in FIG. 10.

Example 9

Preparation of Solvate Form $\varepsilon_1$ of Eluxadoline.

One gram of eluxadoline 2-propanol solvate prepared according to example 13 below was suspended in 10 mL of acetone at 20-25° C. in a glass flask equipped with a magnetic stirrer thermometer, magnetic stirrer and condenser. The resulting suspension was maintained under stirring at the same temperature for 8 hours. The solid was filtered a, thus affording crystalline form $\varepsilon_1$ of eluxadoline as a white solid.

The product is characterized by XRPD, DSC and TGA spectra corresponding to those obtained in example 1.

Example 10

Preparation of the Polymorphically and Chemically Stable Form α' of Eluxadoline.

Eluxadoline form $\varepsilon_1$ was dried under reduced pressure (about $2 \cdot 10^3$ Pa) for 16 hours at 40° C., thus affording particles of the polymorphically and chemically stable crystalline form α' of eluxadoline with a D10 value of 3 μm, a D50 value of 8 μm and a D90 value of 15 μm and a span of 1.5.

The measured melting point was from 189 to 191° C. with no degradation.

Figure 11:
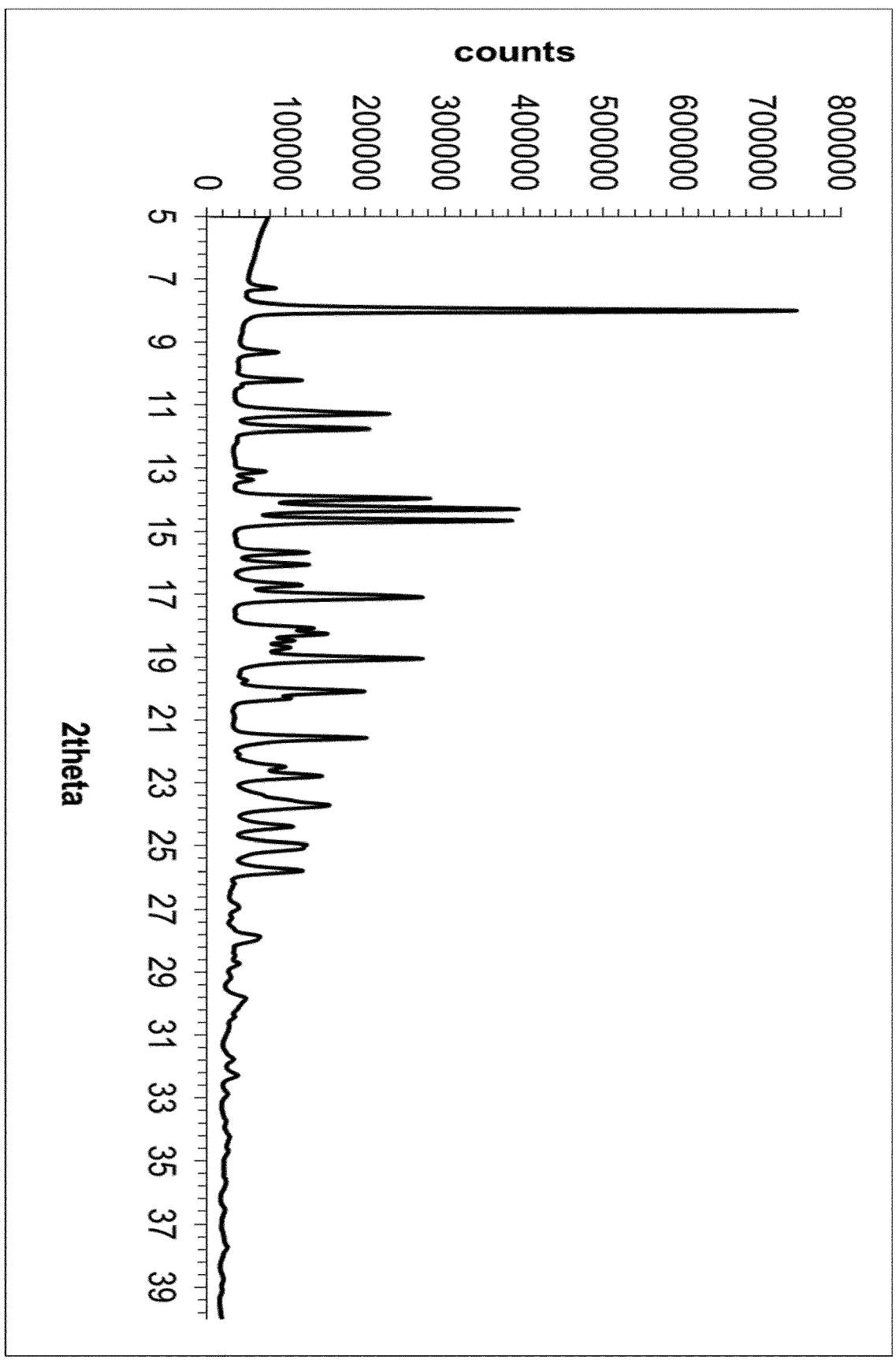
FIG. 11 depicts the X-Ray powder diffractogram of the polymorphically and chemically stable form α' of eluxadoline.

The obtained product was analysed by XRPD, obtaining the diffractogram shown in FIG. 11.

The product was also subjected to DSC, TGA, DVS and SEM analyses, which gave as result the graphs shown in FIGS. 12, 13, 14 and 15.

A portion of the product was subjected to a dissolution test in 50 mM phosphate buffer at pH=7.4 giving the results summarised below:

| Time (min.) | % dissolved |
|---|---|
| 5 | 6.06 |
| 10 | 13.93 |
| 20 | 17.81 |
| 30 | 27.87 |
| 45 | 38.40 |
| 60 | 60.17 |

Example 11

Preparation of the Polymorphically and Chemically Stable Form α' of Eluxadoline.

Eluxadoline form $\varepsilon_2$ was dried under reduced pressure (about $2 \cdot 10^3$ Pa) for 16 hours at 50° C., thus affording the polymorphically and chemically stable crystalline form α' of eluxadoline.

The product is characterized by XRPD, DSC, DVS and TGA spectra corresponding to those obtained in example 10.

Example 12

Preparation of the Polymorphically and Chemically Stable Form α' of Eluxadoline.

Eluxadoline form $\varepsilon_3$ was dried under reduced pressure (about $2 \cdot 10^3$ Pa) for 16 hours at 50° C., thus affording the polymorphically and chemically stable crystalline form α' of eluxadoline.

The product is characterized by XRPD, DSC, DVS and TGA spectra corresponding to those obtained in example 10.

Example 13

Preparation of the 2-Propanol Solvate of Eluxadoline.

One gram of eluxadoline in amorphous form was suspended in 10 mL of 2-propanol at 20-25° C. in a glass flask equipped with thermometer, magnetic stirrer and condenser. Under stirring, the suspension was heated to 60° C. and maintained under these conditions for 8 hours. After cooling down to 20-25° C., filtering, washing with 2-propanol and drying at 35-40° C. in vacuo, 0.85 g of the title compound in the form of a solvate with 2-propanol were obtained.

The obtained product was analysed by XRPD, obtaining the diffractogram shown in FIG. 16.

Figure 17:
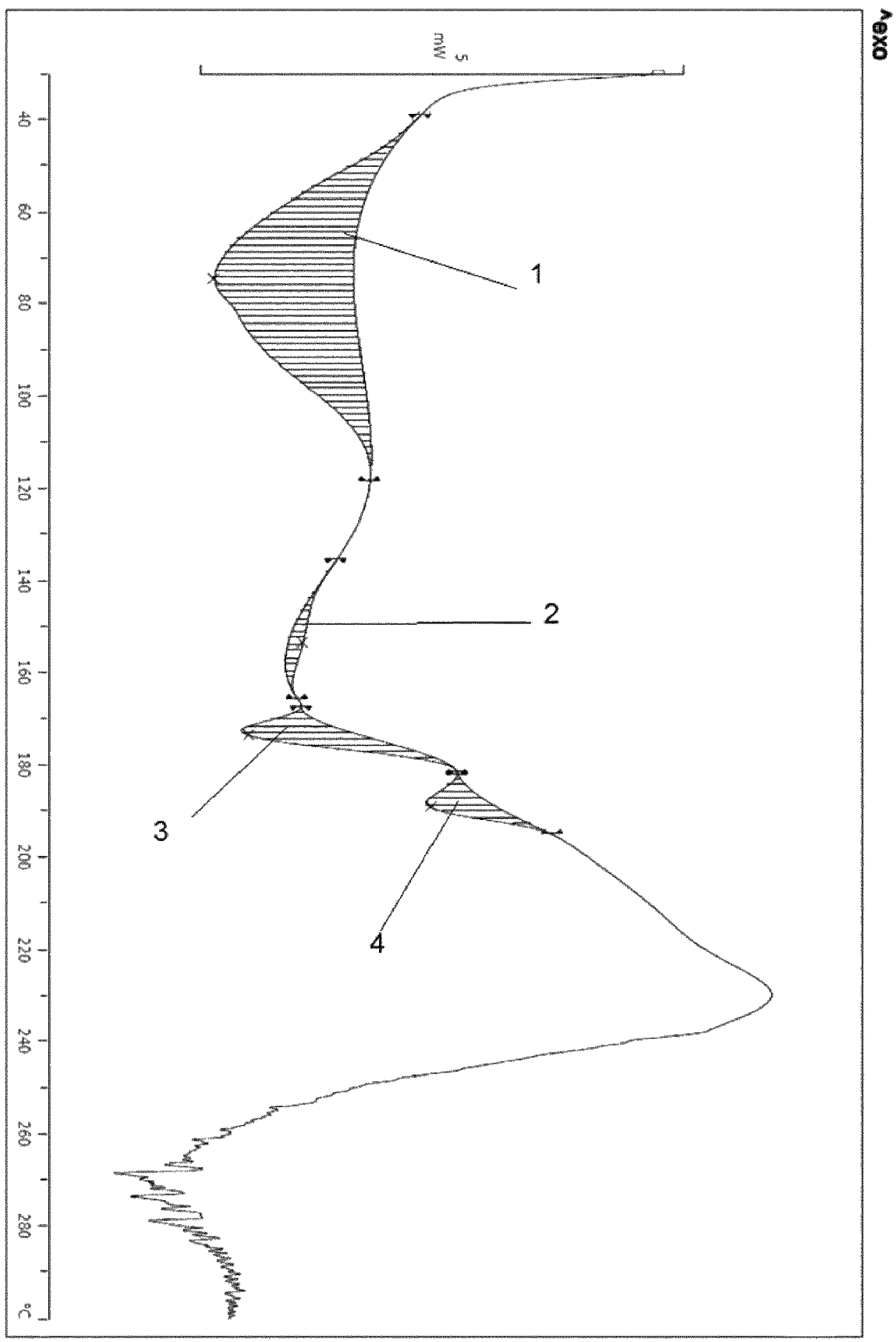
FIG. 17 provides a DSC thermogram of the isomorphous solvate form of eluxadoline prepared according to example 13.
Figure 18:
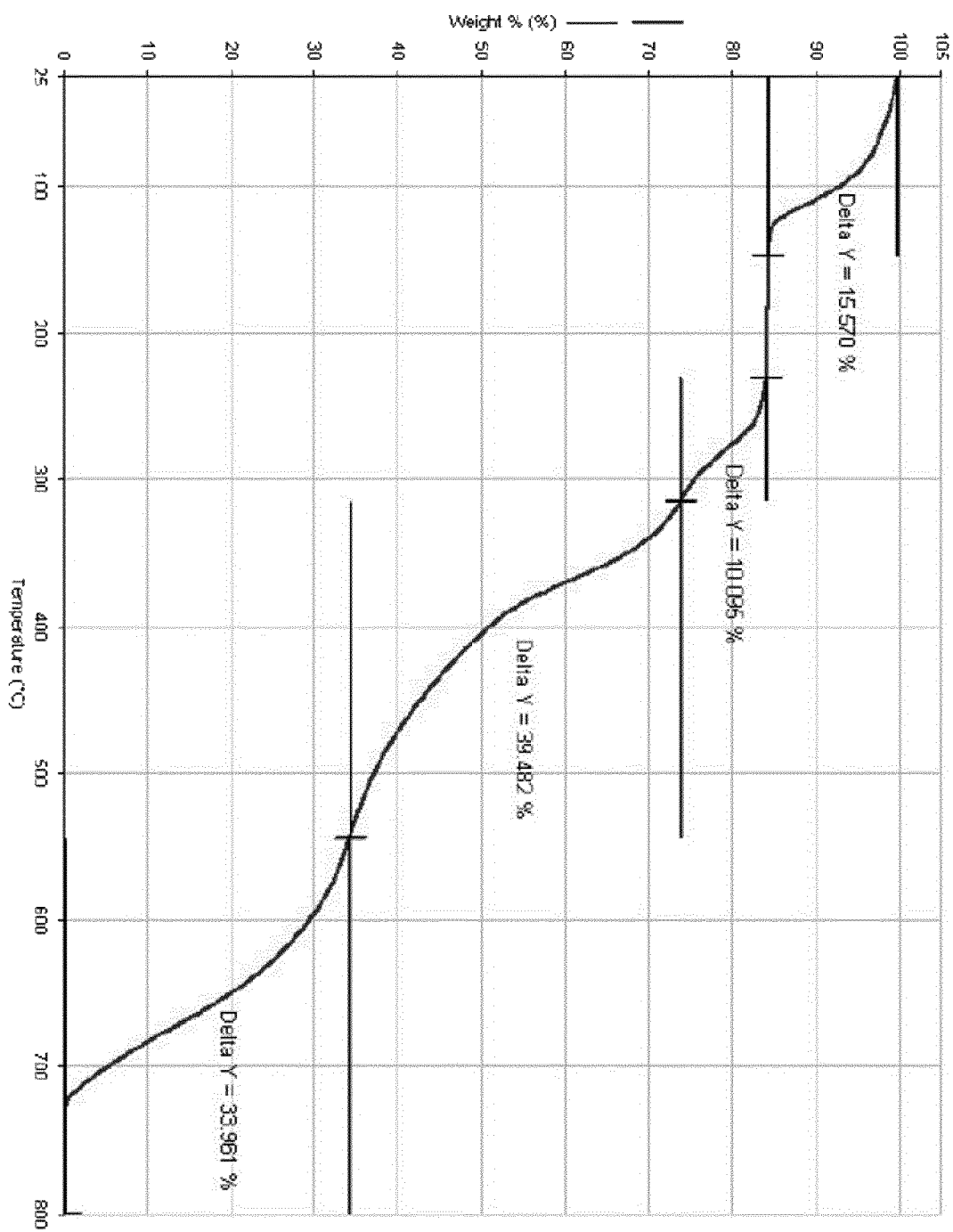
FIG. 18 provides a TGA thermogram of the isomorphous solvate form of eluxadoline prepared according to example 13.

The product was also subjected to DSC and TGA analyses, which gave as results the graphs shown in FIGS. 17 and 18, respectively. The DSC profile is mainly characterized by a broad endothermic band with onset at 44.7° C., related to the loss of solvent. The same loss is evidenced by TGA screening between 25 and 120° C.

FIG. 17 shows the following data:
(1): Integral −326.98 mJ, normalized −49.24 Jg$^{-1}$, Onset 44.71° C., Peak 74.51° C., Left Limit 38.97° C., Right Limit 118.37° C.,
(2) Integral 12.56 mJ, normalized 1.89 Jg$^{-1}$, Onset 140.56° C., Peak 153.33° C., Left Limit 135.31° C., Right Limit 165.24° C.;
(3) Integral −45.74 mJ, normalized −6.89 Jg$^{-1}$, Onset 168.09° C., Peak 173.29° C., Left Limit 166.94° C., Right Limit 181.71° C.;
(4) Integral −26.40 mJ, normalized −3.98 Jg$^{-1}$, Onset 182.65° C., Peak 189.04° C., Left Limit 181.43° C., Right Limit 195.04° C.

A $^1$H NMR analysis of a portion of the product was carried out for estimating the amount of residual solvents, giving as result the presence in the sample of 17.2% by weight of 2-propanol.

Finally, on portions of the sample were carried out a melting point measure and a Karl Fisher assay: the measured melting point was 189° C., while the resulting water content was 0.45% by weight. Melting takes place with no degradation, namely, no browning or other colour change, nor phenomena linked to the evolution of gases, are observed.

Example 14

Preparation of a Mixed 2-Propanol/Water Solvate of Eluxadoline.

One gram of eluxadoline in amorphous form was suspended in 5 mL of 2-propanol and 5 mL of water at 20-25° C. in a glass flask equipped with thermometer, magnetic stirrer and condenser. Under stirring, the suspension was heated up to 60° C. obtaining a clear solution. The obtained solution was allowed to cool down spontaneously to 20-25° C. and seeded with the solid obtained according to Example 13. Suspension was maintained under stirring at 20-25° C. for 8 hours. After filtering, washing with 2-propanol and then drying at 35-40° C. in vacuo, 0.34 g of the title compound in the form of a mixed solvate with water/2-propanol were obtained.

Figure 19:
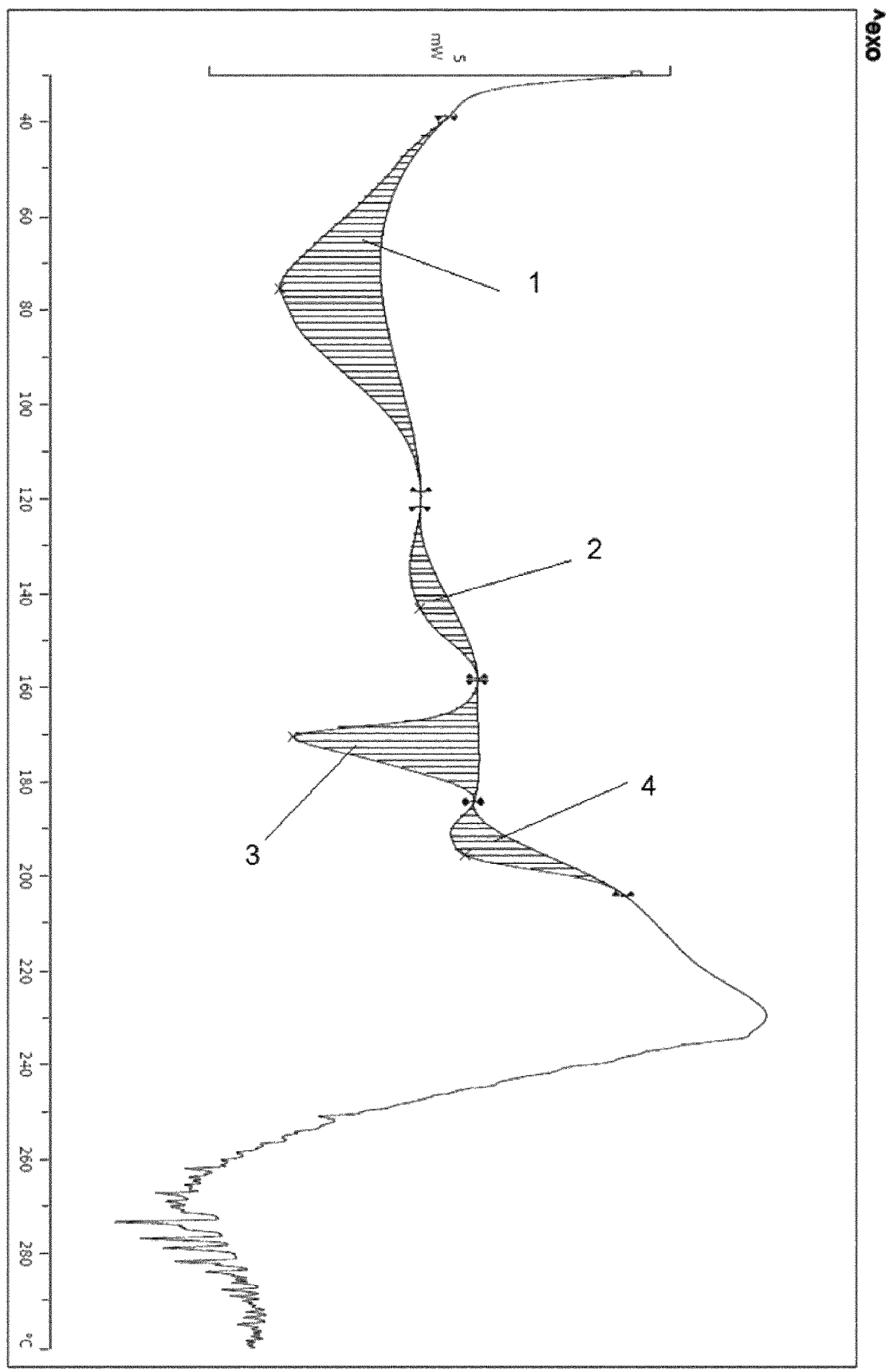
FIG. 19 provides a DSC thermogram of the isomorphous solvate form of eluxadoline prepared according to example 14.
Figure 20:
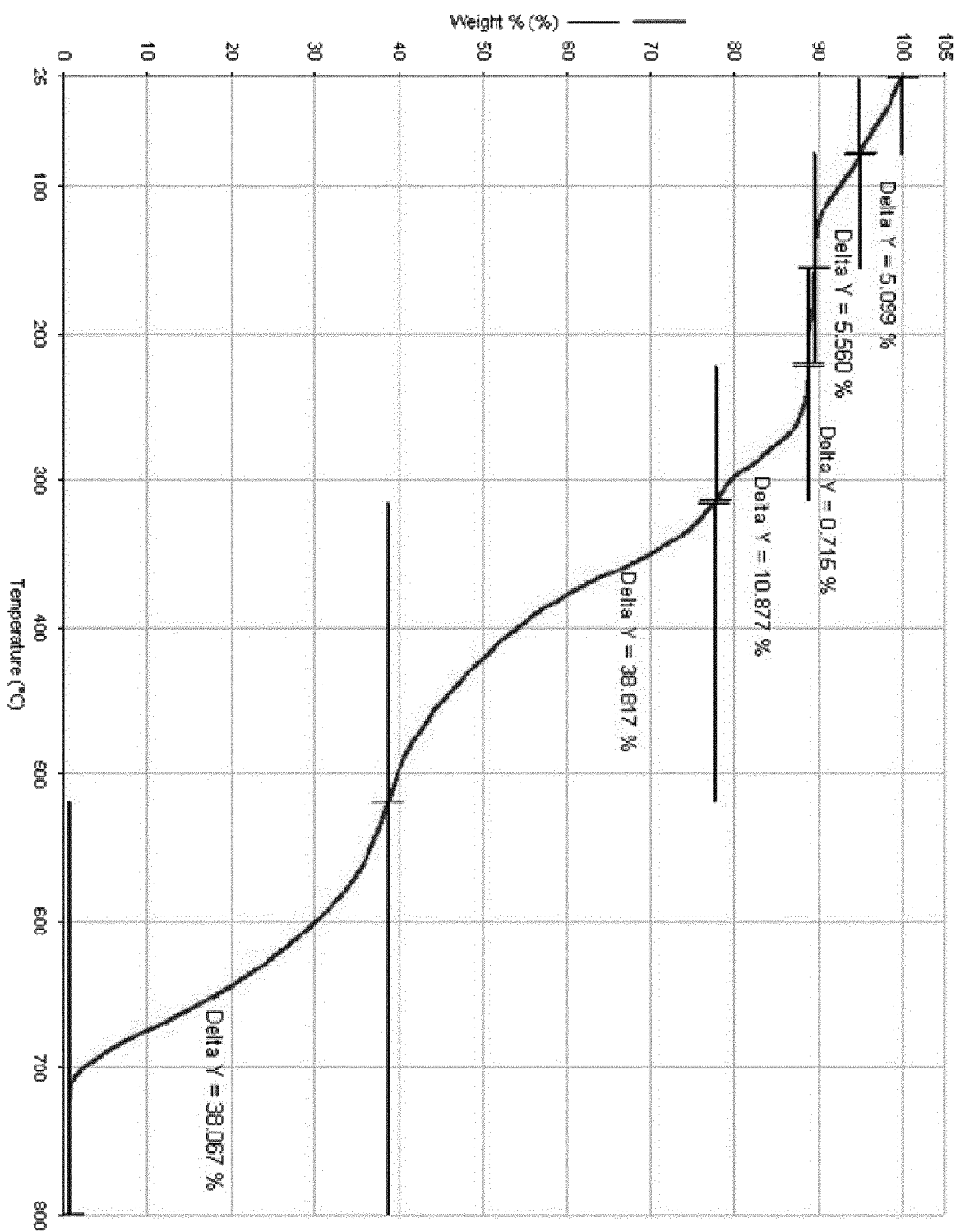
FIG. 20 provides a TGA thermogram of the isomorphous solvate form of eluxadoline prepared according to example 14.

The product was subjected to the same set of analyses of Example 1, obtaining the following results:
XRPD: the diffractogram shows peaks at angles corresponding to the diffractogram of FIG. 16;
DSC: graph shown in FIG. 19;
FIG. 19 shows the following data:
(1): Integral −220.45 mJ, normalized −38.01 Jg$^{-1}$, Onset 39.40° C., Peak 75.37° C., Left Limit 38.98° C., Right Limit 118.39° C.,
(2) Integral −39.75 mJ, normalized −6.85 Jg$^{-1}$, Onset 123.62° C., Peak 143.05° C., Left Limit 121.78° C., Right Limit 157.70° C.;
(3) Integral −110.34 mJ, normalized −19.02 Jg$^{-1}$, Onset 165.60° C., Peak 170.32° C., Left Limit 158.55° C., Right Limit 183.98° C.;
(4) Integral −47.28 mJ, normalized −8.15 Jg$^{-1}$, Onset 184.86° C., Peak 195.39° C., Left Limit 184.27° C., Right Limit 203.85° C.
TGA: graph shown in FIG. 20;
$^1$H NMR: presence of 7.1% by weight of 2-propanol
Melting point: 198° C. with no degradation;
Karl Fisher assay: 4.84% by weight of water.

Example 15

Preparation of the Tetrahydrofuran Solvate of Eluxadoline.

Eluxadoline form $\varepsilon_1$ obtained according to Example 1 was suspended in 10 mL of tetrahydrofuran (THF) at 20-25° C. in a glass flask equipped with a magnetic stirrer, and kept in these conditions over 8 hours. The slurry led to the loss of trapped acetone, as confirmed by $^1$H-NMR, and its substitution with included THF.

The product, after isolation, was subjected to XRPD analysis, obtaining a diffractogram showing peaks at angles corresponding to the diffractogram of FIG. 16.

Example 16

Preparation of the Tert-Butanol Solvate of Eluxadoline.

Eluxadoline form $\varepsilon_1$ obtained according to Example 1 was suspended in 10 mL of tert-butanol (t-BuOH) at 20-25° C. in a glass flask equipped with a magnetic stirrer, and kept in these conditions over 16 hours. The slurry led to the loss of trapped acetone, as confirmed by $^1$H-NMR, and its substitution with included t-BuOH.

The product, after isolation, was subjected to XRPD analysis, obtaining a diffractogram showing peaks at angles corresponding to that obtained in example 15.

Example 17

Preparation of the Ethanol Solvate of Eluxadoline.

Eluxadoline form $\varepsilon_1$ obtained according to Example 1 was suspended in 20 mL of ethanol at 20-25° C. in a glass flask equipped with thermometer, magnetic stirrer and condenser. Under stirring, the suspension was heated up to reflux temperature (78° C.) and maintained under these conditions over 8 hours. The slurry led to the loss of trapped acetone, as confirmed by $^1$H-NMR, and its substitution with included ethanol.

The product, after isolation, was subjected to XRPD analysis, obtaining a diffractogram showing peaks at angles corresponding to that obtained in example 15.

The product was subjected to the following analyses:
$^1$H NMR: presence of 18.8% by weight of ethanol
Karl Fisher assay: 0.28% by weight of water.

Example 18

Thermal Stability of the Polymorphically and Chemically Stable Form α' of Eluxadoline The polymorphically and chemically stable form α' of eluxadoline, prepared as described in Examples 10 to 12, were maintained at 120° C. for 24 or 48 hours. Then they were cooled to room temperature and subjected to XRPD analysis, giving rise to a XRPD spectrum corresponding to the one obtained in example 10.

Example 19

Chemical Stability of the Polymorphically and Chemically Stable Form α' of Eluxadoline The polymorphically and chemically stable form α' of eluxadoline, prepared as described in Example 10, was maintained at 120° C. for 24 or 48 hours. Then they were cooled to room temperature and subjected to HPLC analysis, giving rise to the results reported below:

| Time | Eluxadoline Retention Time: about 9.6 Relative Retention Time: 1.00 | Impurity (A%) Retention Time: about 10.7 Relative Retention Time: 1.11 |
|---|---|---|
| 0 | 99.77 | 0.04 |
| 24 hours | 99.62 | 0.18 |
| 48 hours | 99.60 | 0.20 |

Example 20

Preparation of the Polymorphically and Chemically Stable Form α' of Eluxadoline. 5.0 g of amorphous Eluxadoline were added under stirring and at 20-25° C. to a mixture comprising 25 mL of ethyl acetate, 25 mL of water and 4.92 g of sodium acetate. The resulting suspension was maintained under stirring under reflux conditions (about 72° C.) for 4 hours. The suspension was cooled to 20-25° C. and maintained in these conditions for additional 16 hours. The attained solid was filtered, washed with water (2×10 mL) and dried at 40° C. under reduced pressure, thus affording 4.21 of the polymorphically and chemically stable form α' of eluxadoline.

The product, after isolation, was subjected to XRPD analysis, obtaining a diffractogram showing peaks at angles corresponding to that obtained in example 10

The invention claimed is:

1. A polymorphically and chemically stable crystalline form α' of 5-({[(2S)-2-amino-3-(4-carbamoyl-2,6-dimethylphenyl)propanoyl][(1S)-1-(4-phenyl-1H-imidazol-2-yl)ethyl]-amino}methyl)-2-methoxybenzoic acid having an X-ray powder diffraction pattern that, when collected with Kα radiation of copper (λ=1.5418 Å) comprises main peaks at 7.98°, 13.94°, 14.28°, 14.66°, and 19.04° 2θ±0.1° 2θ.

Figure 14:
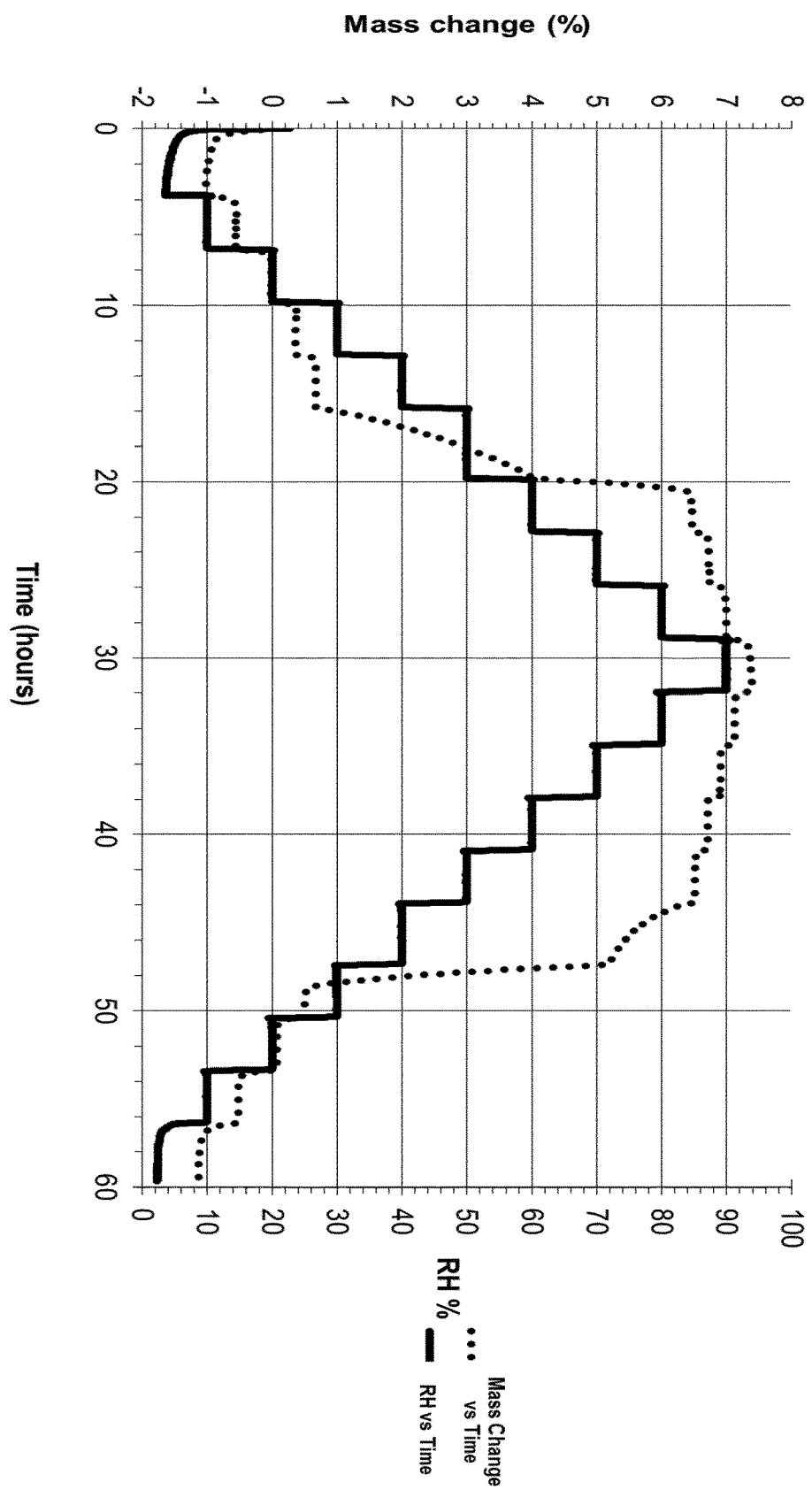
FIG. 14 depicts a DVS isotherm of the polymorphically and chemically stable form α' of eluxadoline.

2. The crystalline form according to claim 1, wherein said crystalline form comprises at least one of features (xi) to (xxi):

(xi) an X-ray powder diffraction pattern that, when collected with Kα radiation of copper (λ=1.5418 Å), is characterized by at least the following main peaks at 7.98°, 11.26°, 13.94°, 14.28°, 14.66°, 17.08°, 19.04% and 21.56° 2θ±0.1° 2θ;

(xii) a DSC thermogram that, when performed with a heating ramp of 10° C./min, comprises an event with a maximum at 198.9° C.±4.0° C.;

(xiii) a DSC thermogram that, when performed with a heating ramp of 10° C./min, comprises a feature with a maximum at 61.2° C.±4.0° C. and an event with a maximum at 198.9° C.±4.0° C.;

(xiv) a TGA thermogram comprising a weight loss step between 25° C. and 80° C. of up to 1%;

(xv) SEM images as depicted in FIG. 15;

(xvi) a particle size distribution with a span of less than 2.5;

(xvii) a melting point from 189 to 191° C.;

(xviii) a DVS isotherm as depicted in FIG. 14;

(xix) a content of the impurity at relative retention time of 1.11 lower than 0.50 A % when exposed to a temperature of 120° C. for 24 hours;

(xx) a content of the impurity at relative retention time of 1.11 lower than 0.50 A % when exposed to a temperature of 120° C. for 48 hours; and (xxi) a combination of any two or more (xi) (xx);

wherein the relative retention times of (xix) and (xx) are determined according to the following conditions:

Column: XBridge C8 150×4.6 mm, 3.5 μm
Mobile Phase A: 0.1% (V/V) phosphoric acid aqueous solution
Mobile Phase B: Acetonitrile
Diluent: 1:1 (V/V) Mixture of Mobile Phases A and B
Flow Rate: 1.3 mL/min
Runtime: 35 min
Column Temperature 30° C.
Autosampler Temperature: Ambient
Injection Volume: 5 μL
Detection: 210 nm
Sample concentration: 0.4 mg/mL
Gradient Program:

| Time (min.) | A (%) | B (%) |
|---|---|---|
| 0 | 95 | 5 |
| 35 | 60 | 40 |
| 36 | 10 | 90 |
| 40 | 10 | 90 |
| 41 | 95 | 5 |
| 55 | 95 | 5. |

3. A solvate form of 5-({[(2S)-2-amino-3-(4-carbamoyl-2,6-dimethylphenyl)propanoyl][(1S)-1-(4-phenyl-1H-imidazol-2-yl)ethyl]amino}methyl)-2-methoxybenzoic acid with a ketone selected from the group consisting of acetone, 2-butanone, 3-pentanone and mixtures thereof.

4. The solvate form according to claim 3, wherein the solvate form is an acetone solvate showing having unit cell parameters equal to the following cell dimensions: a=24.18 Å±0.01 Å; b=17.10 Å±0.01 Å, c=9.62 Å±0.01 Å; α=90 degrees, β=90 degrees; γ=90 degrees.

5. The solvate form according to claim 4, wherein the solvate form in an X-ray powder diffraction pattern collected with Kα radiation of copper (λ=1.5418 Å) comprises main peaks at 6.33°, 8.92°, 9.86°, 12.80°, and 18.04°±0.1° 2θ.

6. The solvate form according to claim 5, wherein the X-ray powder diffraction pattern further comprises peaks at 7.28°, 8.92°, 13.82% and 15.06°±0.1° 2θ.

7. The solvate form according to claim 4, wherein the solvate form in a DSC thermogram performed with a heating ramp of 10° C./min comprises a first feature with maximum at 122.9° C.±4.0° C., an event with maximum at 173.7° C.±4.0° C., and a second feature with maximum at 196.6° C.±4.0° C.

8. The solvate form according to claim 4, wherein the solvate form in a TGA thermogram shows a weight loss step between 25° C. and 120° C. of up to 16.0%.

9. The solvate form according to claim 3, wherein the solvate is a 2-butanone solvate having unit cell parameters equal to the following cell dimensions a=24.17 Å±0.01 Å; b=17.05 Å±0.01 Å, c=9.69 Å±0.01 Å; α=90 degrees, β=90 degrees; γ=90 degrees.

10. The solvate form according to claim 9, wherein in an X-ray powder diffraction pattern that is collected with Kα radiation of copper (λ=1.5418 A), the solvate form comprises main peaks at 6.32°, 8.94°, 10.98°, 12.78°, and 18.02°±0.1° 2θ.

11. The solvate form according to claim 9, wherein the solvate form in a DSC thermogram that, when performed with a heating ramp of 10° C./min, comprises a feature with a maximum at 137.7° C.±4.0° C., an event with a maximum at 173.6° C.±4.0° C. and a feature with a maximum at 196.9° C.±4.0° C.

12. The solvate form according to claim 3, wherein the solvate is a 3-pentanone solvate having unit cell parameters equal to the following cell dimensions a=23.88 Å±0.01 Å; b=17.13 Å±0.01 Å, c=9.76 Å±0.01 Å; α=90 degrees, β=90 degrees; γ=90 degrees.

13. The solvate form according to claim 12, wherein in an X-ray powder diffraction pattern that is collected with Kα radiation of copper (λ=1.5418 Å), is characterized by at least the following the solvate form comprises main peaks at 6.36°, 11.00°, 12.80°, 18.16% and 23.18°±0.1° 2θ.

14. The solvate form according to claim 13, wherein the solvate form in a DSC thermogram performed with a heating ramp of 10° C./min comprises a first feature with a maximum at 122.9° C.±4.0° C., an event with a maximum at 173.7° C.±4.0° C., and a second feature with a maximum at 196.6° C.±4.0° C.

15. A pharmaceutical composition comprising, as active ingredient, an effective amount of the crystalline form according to claim 1 and at least one pharmaceutically acceptable excipient.

16. A pharmaceutical composition comprising, as active ingredient, an effective amount of the crystalline form according to claim 3 and at least one pharmaceutically acceptable excipient.

* * * * *